(12) United States Patent
Harth

(10) Patent No.: US 12,138,347 B2
(45) Date of Patent: Nov. 12, 2024

(54) NANOPARTICLES AND NANONETWORKS FORMED THEREFROM

(71) Applicant: University of Houston System, Houston, TX (US)

(72) Inventor: Eva Harth, Houston, TX (US)

(73) Assignee: University of Houston System, Houston, TX (US)

(*) Notice: Subject to any disclaimer, the term of this patent is extended or adjusted under 35 U.S.C. 154(b) by 623 days.

(21) Appl. No.: 17/291,079

(22) PCT Filed: Nov. 5, 2019

(86) PCT No.: PCT/US2019/059763
§ 371 (c)(1),
(2) Date: May 4, 2021

(87) PCT Pub. No.: WO2020/097009
PCT Pub. Date: May 14, 2020

(65) Prior Publication Data
US 2021/0401750 A1    Dec. 30, 2021

Related U.S. Application Data

(60) Provisional application No. 62/755,611, filed on Nov. 5, 2018.

(51) Int. Cl.
| | | |
|---|---|---|
| A61K 9/16 | (2006.01) | |
| A61K 31/337 | (2006.01) | |
| A61K 31/365 | (2006.01) | |
| A61K 31/366 | (2006.01) | |
| A61K 31/40 | (2006.01) | |
| A61K 31/4745 | (2006.01) | |
| A61K 31/519 | (2006.01) | |

(Continued)

(52) U.S. Cl.
CPC .......... *A61K 9/1647* (2013.01); *A61K 31/337* (2013.01); *A61K 31/365* (2013.01); *A61K 31/366* (2013.01); *A61K 31/40* (2013.01); *A61K 31/4745* (2013.01); *A61K 31/519* (2013.01); *A61K 31/58* (2013.01); *A61K 31/704* (2013.01)

(58) Field of Classification Search
CPC .. A61K 9/1647; A61K 31/337; A61K 31/365; A61K 31/366; A61K 31/40; A61K 31/4745; A61K 31/519; A61K 31/58; A61K 31/704
See application file for complete search history.

(56) References Cited

U.S. PATENT DOCUMENTS

| | | |
|---|---|---|
| 2003/0004217 A1 | 1/2003 | Kawamoto et al. |
| 2015/0087790 A1 | 3/2015 | Harth et al. |

(Continued)

FOREIGN PATENT DOCUMENTS

| | | |
|---|---|---|
| WO | 0061667 A1 | 10/2000 |
| WO | 2017081069 A1 | 5/2017 |

OTHER PUBLICATIONS

International Search Report and Written Opinion of the International Searching Authority issued in corresponding Application No. PCT/US19/59763 mailed Jan. 17, 2020 (10 pages).

*Primary Examiner* — Jianfeng Song
(74) *Attorney, Agent, or Firm* — Carter, DeLuca & Farrell, LLP; George Likourezos, Esq.

(57) ABSTRACT

Nanoparticles and nanonetworks formed of these nanoparticles are provided. Methods for forming such nanoparticles and nanonetworks are also provided, as well as uses of the nanoparticles and/or nanonetworks, including their use for drug delivery.

3 Claims, 18 Drawing Sheets

(51) Int. Cl.
*A61K 31/58* (2006.01)
*A61K 31/704* (2006.01)

(56) References Cited

U.S. PATENT DOCUMENTS

| | | |
|---|---|---|
| 2016/0237208 A1 | 8/2016 | Harth et al. |
| 2018/0142061 A1 | 5/2018 | Harth et al. |

FIG. 1. 400 MHz $^1$H NMR spectra of VL-co-OPD in CDCl$_3$.

FIG. 2. 400 MHz $^1$H NMR characterization of ketoxime nanoparticles in $CDCl_3$.

FIG. 3. 400 MHz $^1$H NMR characterization of alkoxyamine nanoparticles in CDCl$_3$.

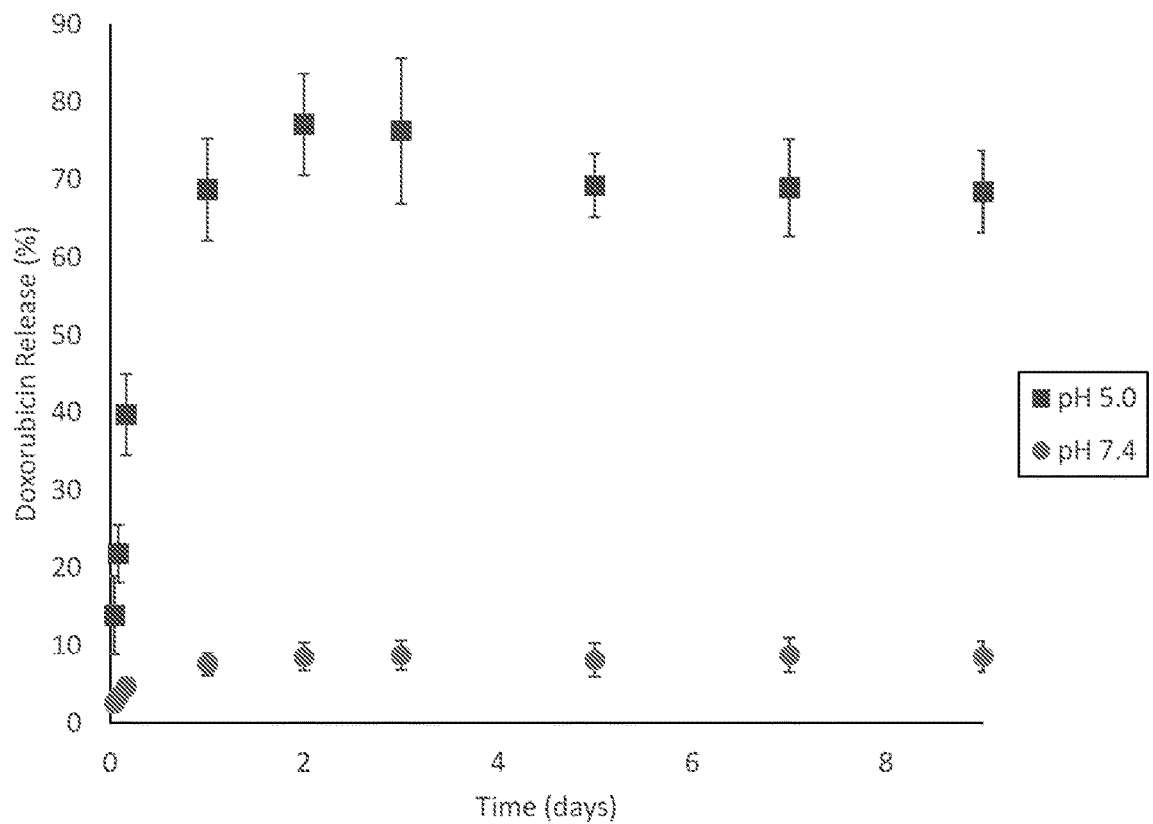
Figure 8: Cumulative release of doxorubicin from polyester partially reduce ketoxime/alkoxyamine nanoparticles (8% OPD, 2.7 mM) in pH 5 (blue squares) and pH 7.4 (red circles) aqueous media at 37 °C for 17 days. Values are averages of measurements in triplicate.

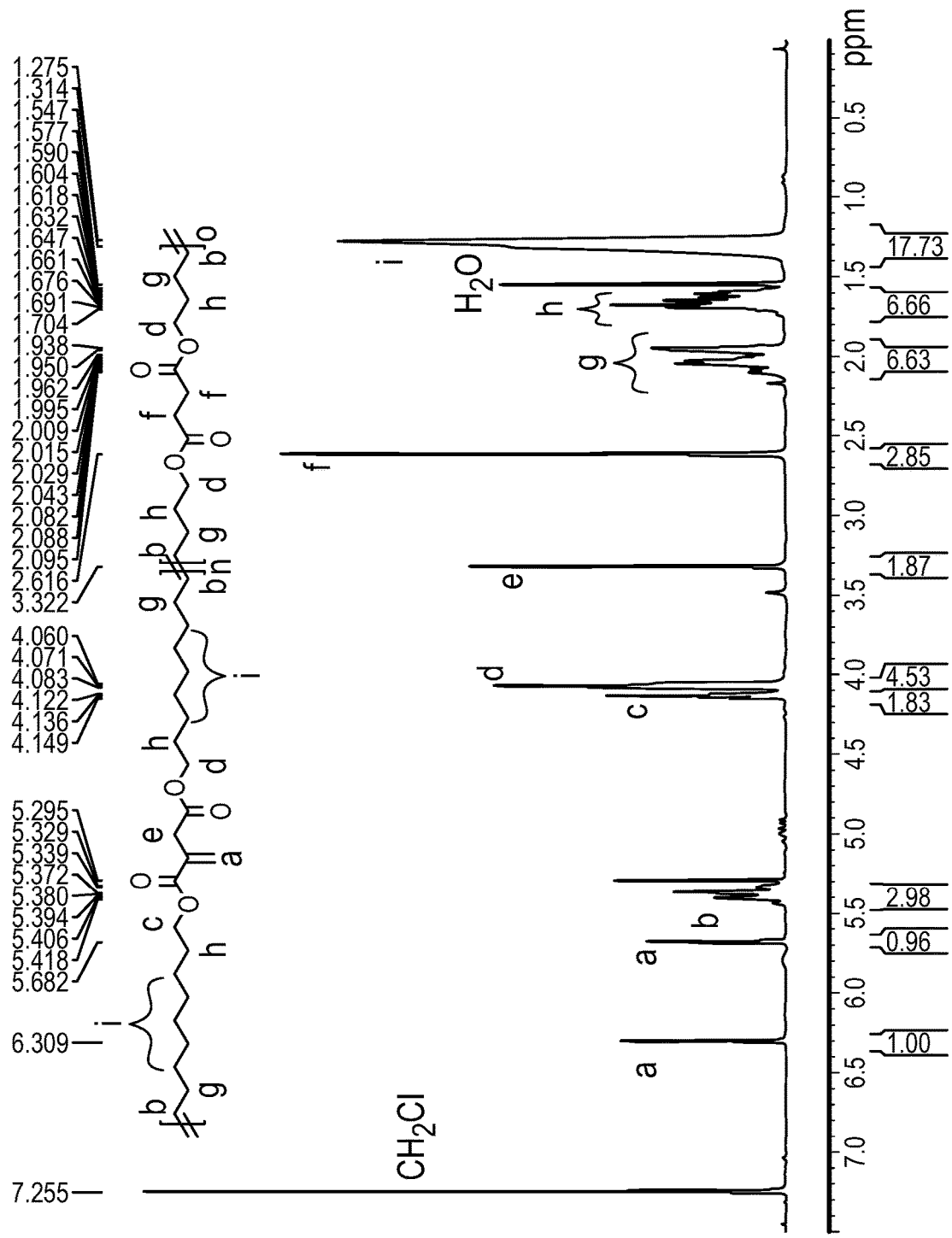
FIG. 9. The $^1$H NMR (CDCl$_3$, 400 MHz) spectrum of P(DDI-co-DPS).

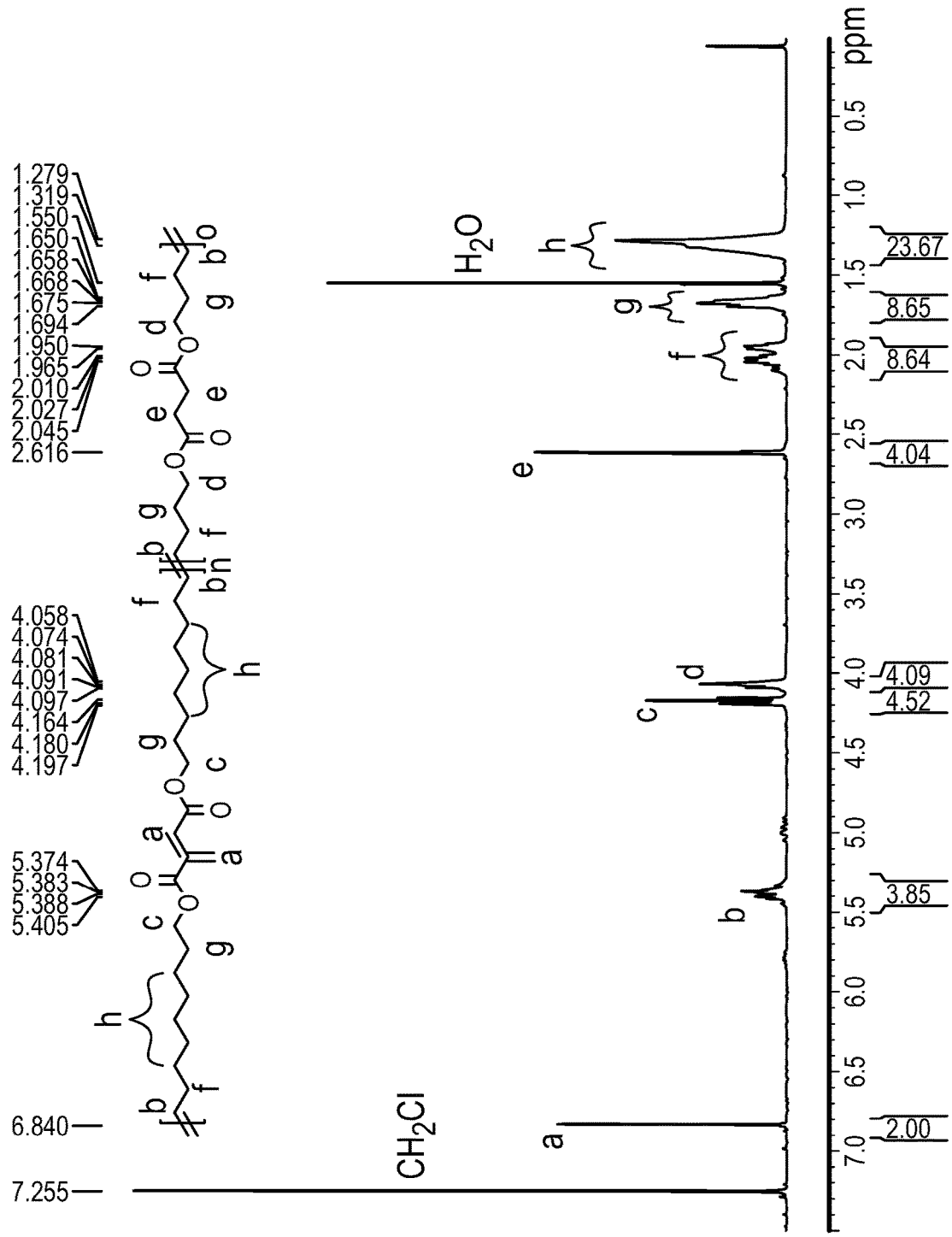
FIG. 10. The $^1$H NMR (CDCl$_3$, 400 MHz) spectrum of P(DDF-co-DPS).

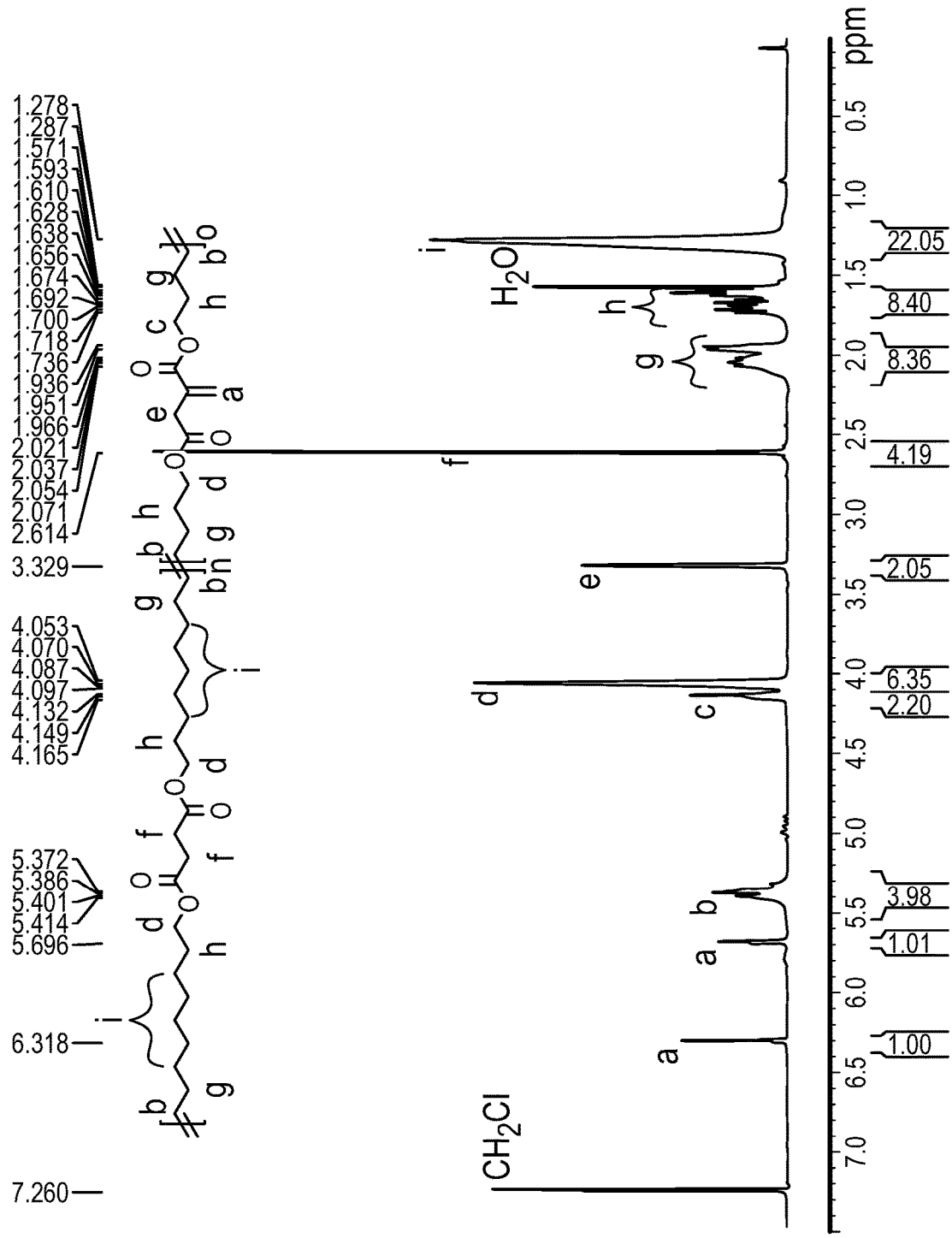
FIG. 11. The $^1$H NMR (CDCl$_3$, 400 MHz) spectrum of P(DDS-co-DPI).

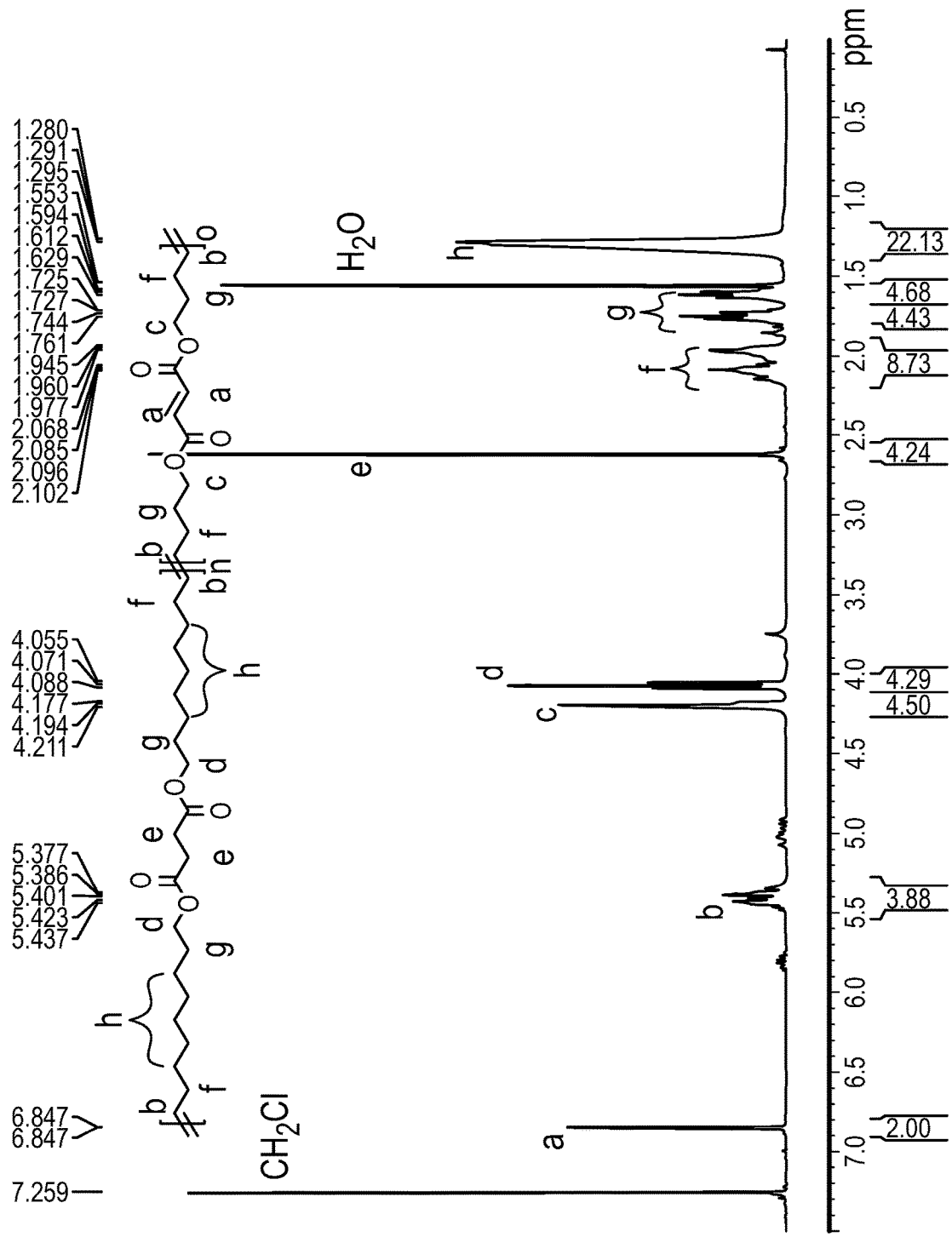
FIG. 12. The $^1$H NMR (CDCl, 400 MHz) spectrum of P(DDS-co-DPF).

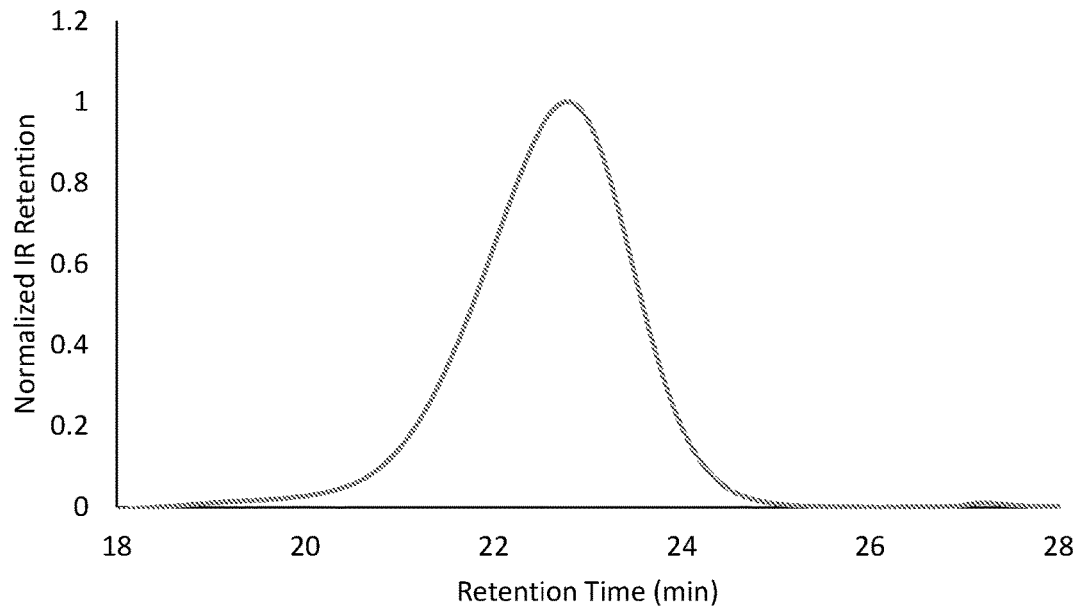
Figure 13. Representative GPC trace of P(DDI-*co*-DPS), measured in THF at 40 °C with a flow rate of 1 mL/min.
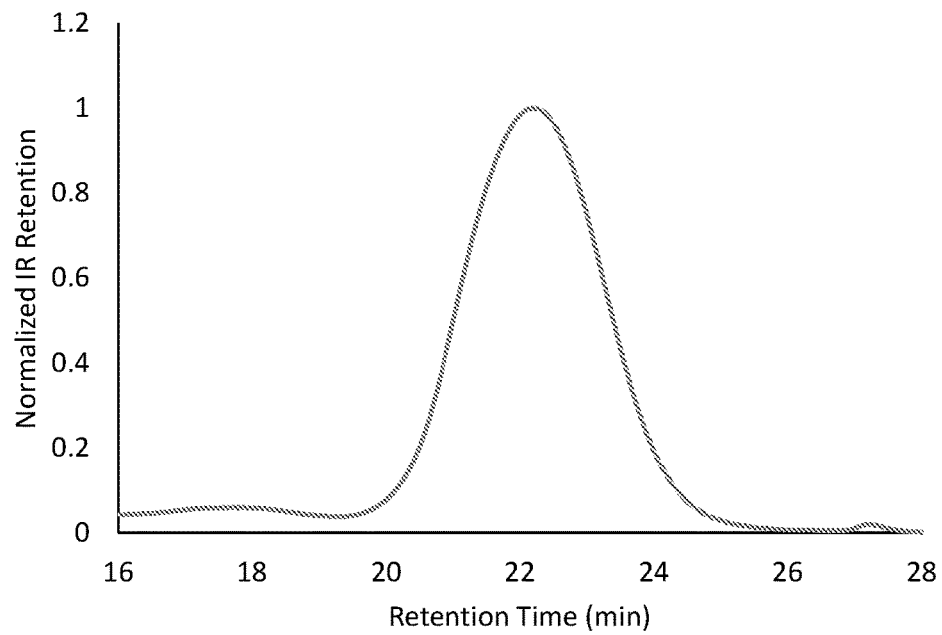
Figure 14. Representative GPC trace of P(DDS-*co*-DPI), measured in THF at 40 °C with a flow rate of 1 mL/min.

NANOPARTICLES AND NANONETWORKS FORMED THEREFROM

CROSS REFERENCE TO RELATED APPLICATIONS

This application is a National Stage of, and claims priority to and the benefit of, International Patent Application No. PCT/US2019/059763, filed Nov. 5, 2019, which, in turn, claims the benefit of, and priority to, U.S. Provisional Patent Application Ser. No. 62/755,611, filed Nov. 5, 2018, the entire disclosures of each of which are incorporated by reference herein.

BACKGROUND

Biodegradable nanoparticles have received increasing attention as versatile drug delivery scaffolds to enhance the efficacy of therapeutics. Effectiveness of delivery, however, can be influenced by the particle size and morphology, as these parameters can greatly affect the biological function and fate of the material.

Many drug delivery systems have been developed, but so far nanodelivery methods are lagging because of the complexity of their design and synthesis. Attempts to simplify the synthesis have met with limited success, as the system has marginal adjustability and is limited in delivery options for bioactive agents.

Improved methods and compositions for producing degradable nanoparticles with reproducibility in particle size and shape remain desirable.

SUMMARY

The present disclosure provides nanoparticles and methods for forming nanonetworks from these particles. The methods of the present disclosure include both a practical approach and the ability to tune and adjust the release profiles of bioactive agents from the nanoparticles and resulting nanonetworks depending on the disease to be treated. The postloading of one or multiple drugs after the particle has been made is another advantage in contrast to other delivery systems.

In embodiments, the present disclosure provides a crosslinking process that does not depend on pendant functional groups and their modification, but rather engages with functional groups as part of the polymer backbone. The reaction is compatible with aqueous and organic environments and rapidly proceeds at room temperature with high fidelity.

In embodiments the integration of ketone functionalities into polymer backbones is conducted by copolymerization of 2-oxepane-1,5-dione (OPD), a 7-membered functionalized lactone. Using these materials, discrete nanoparticles are synthesized utilizing oxime-click chemistry to produce particles of discrete sizes and crosslinking densities.

The ketoxime bond is generated from ketone functional groups integrated in the polyester backbone, to yield either pH-responsive nanonetworks or pH-stable nanoparticles with alkoxyamine bonds after postmodification reactions. The presented two- or three-step synthetic process is ideal to tune the dimension and network densities, degradation and drug release of the particles to prepare a range of delivery systems in a facile manner.

Other functional groups as part of the polymer backbones are based on itaconate and fumarate functionalities to form polymer networks with difunctionalized crosslinker with amine and thiol end functionalities as described in greater detail below and as depicted in the Figures.

In embodiments, a therapeutic composition of the present disclosure includes a modified polyester having functional groups within the polyester backbone; a crosslinking agent; and a bioactive agent, wherein the crosslinking agent reacts with the functional groups within the polyester backbone to form bonds beween multiple polyester backbones, thereby forming a nanoparticle.

In some embodiments the polyester backbone possesses a ketone functional group.

In embodiments the crosslinking agent is selected from primary amines, secondary amines, alkoxy amines, alcohols, combinations thereof, and the like.

In some embodiments, crosslinking the ketone in the polyester backbone forms a ketoxime bond.

In embodiments the polyester backbone is formed of monomers including itaconate, fumarate, and combinations thereof. In some embodiments, the polyester backbone further includes a succinate. The crosslinking agent may be selected from amines, primary amines, secondary amines, alkoxy amines, alcohols, thiols, and combinations thereof.

In embodiments, the bioactive agent is selected from Brefeldin A, doxorubicin, atorvastatin, simvastatin, methotrexate, finasteride, camptothecin, taxol, photoactive compounds, dyes, fluorescent compounds, porphyrin based compounds, cis-platinum compounds, metallo-organic compounds, and combinations thereof.

In some embodiments the nanoparticle reacts with other nanoparticles to form a nanosponge possessing the bioactive agent. The nanosponge may possess the bioactive agent in an amount from about 1% by weight of the nanosponge to about 25% by weight of the nanosponge.

In other embodiments, a therapeutic composition of the present disclosure includes a modified polyester having a ketone functional groups within the polyester backbone; a crosslinking agent; and a bioactive agent, wherein the crosslinking agent reacts with the functional groups within the polyester backbone to form bonds beween multiple polyester backbones, thereby forming a nanoparticle.

In other embodiments, a therapeutic composition of the present disclosure includes a modified polyester having functional groups within the polyester backbone, the polyester backbone possessing monomers selected from itaconate, fumarate, and combinations thereof; a crosslinking agent selected from amines, primary amines, secondary amines, alkoxy amines, alcohols, thiols, and combinations thereof; and a bioactive agent, wherein the crosslinking agent reacts with the functional groups within the polyester backbone to form bonds beween multiple polyester backbones, thereby forming a nanoparticle.

In some embodiments, the polyester backbone further includes a succinate.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 8 is a graph depicting the cumulative release of doxorubicin from polyester partially reduce ketoxime/alkoxyamine nanoparticles (8% OPD, 2.7 mM) in pH 5 (squares) and pH 7.4 (circles) aqueous media at 37° C. for 17 days;

FIG. 9 is a $^1$H NMR (CDCl$_3$, 400 MHz) spectrum of P(DDI-co-DPS);

FIG. 10 is a $^1$H NMR (CDCl$_3$, 400 MHz) spectrum of P(DDF-co-DPS);

FIG. 11 is a $^1$H NMR (CDCl$_3$, 400 MHz) spectrum of P(DDS-co-DPI);

FIG. 12 is a $^1$H NMR (CDCl$_3$, 400 MHz) spectrum of P(DDS-co-DPF);

FIG. 13 is a representative GPC trace of P(DDI-co-DPS), measured in THF at 40° C. with a flow rate of 1 mL/min.;

FIG. 14 is a representative GPC trace of P(DDS-co-DPI), measured in THF at 40° C. with a flow rate of 1 mL/min.

DETAILED DESCRIPTION

Figure 1:
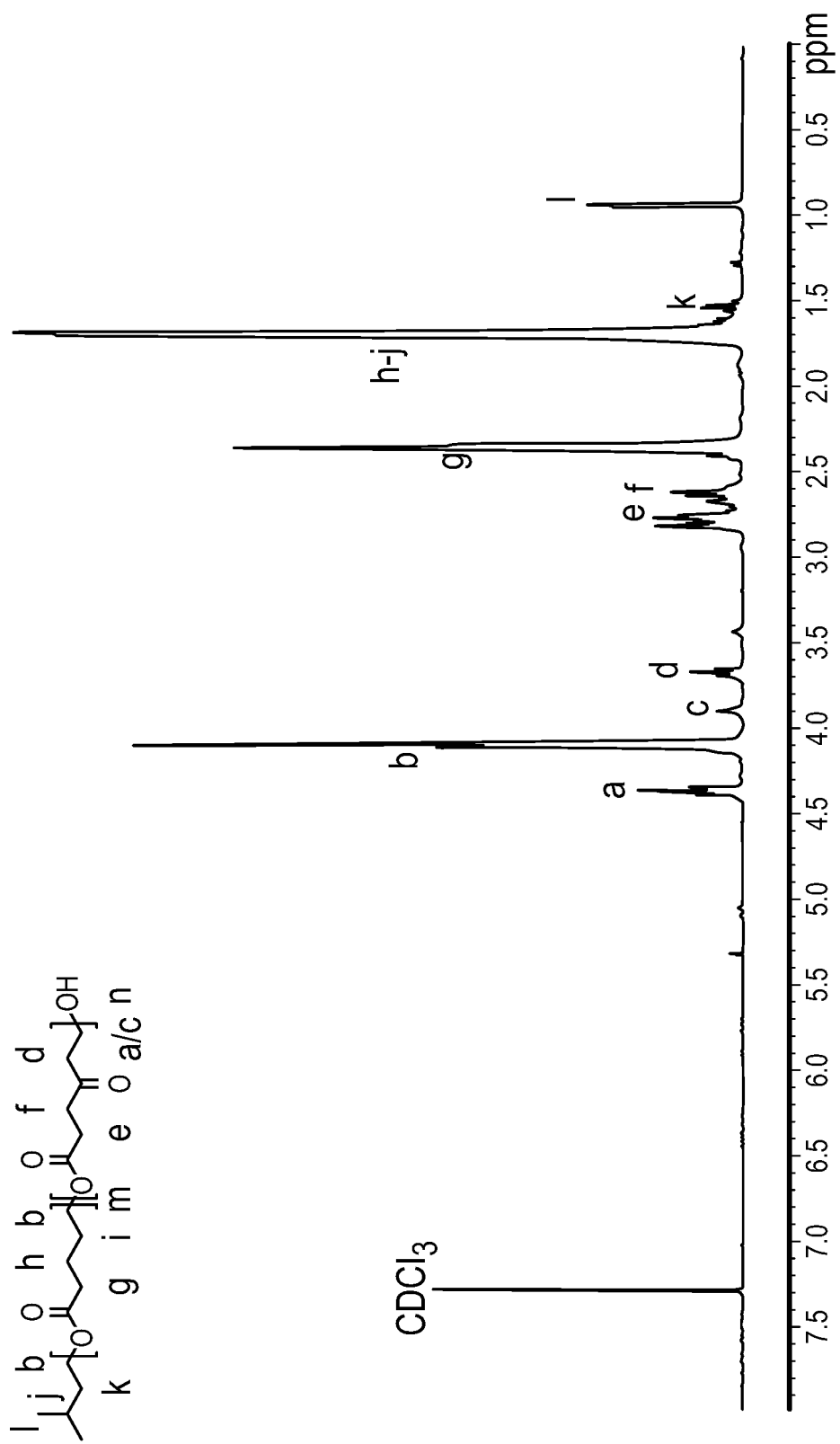
FIG. 1 is a 400 MHz $^1$H NMR spectra of VL-co-OPD in $CDCl_3$.

The present disclosure provides nanonetwork materials, sometimes referred to, in embodiments, as nanosponges. Previous methods for forming these materials included crosslinking of pendant functional groups such as epoxides with nucleophiles. The amount of pendant groups per chain and the amount of crosslinker governed size and network density control, which were important factors to control the release of therapeutics from the nanonetwork materials. The nanonetwork allowed for postloading with drugs, another advantage with the design of scalable drug delivery systems.

The present disclosure provides an even more practical synthesis route by incorporating crosslinking units into the backbone of the polymer chain, rather than generating pendant functional groups through postmodification chemistries. In embodiments, the present disclosure includes a polymer having functional groups within its backbone, rather than pendant functional groups that are often used in the art. In some embodiments, the polymer used is a polyester.

In accordance with the present disclosure, in embodiments a keto group is introduced into the polymer backbone, which then facilitates formation of a ketoxime bond with aminooxy groups to link the backbone with other backbones. In some embodiments, the ketoxime bond with aminooxy groups can be then reduced to an alkoxyamine bond in a consecutive one step procedure.

In contrast to previous work forming nanonetworks from linear components with pendant reactivity, the reactive ketone functional group is part of the polymer backbone. In embodiments, this reactive functional group may be introduced into the polymer backbone by copolymerization of 2-oxepane-1,5-dione (OPD) monomers together with δ-valerolactone. This process precludes post-polymerization reactions, modifying pendant functional groups in the polyester component, and provides direct access to the crosslinking entity.

The concentration of the monomer, in embodiments OPD unit, in solution, is an important factor contributing to the controlled production of these particles. As set forth in greater detail below, conditions were investigated to yield a set of six particles in well-defined dimensions ranging from 39 nm to 173 nm.

Suitable crosslinking agents for forming the nanoparticles of the present disclosure and subsequent nanosponges will depend on the functional group within the polymer backbone. For example, where the polymer backbone is formed using OPD and a lactone, suitable crosslinking agents include primary amines forming imine derivatives, secondary amines forming enamine derivatives, alkoxy amines forming oximes, alcohols forming acetals, combinations thereof, and the like. Exemplary amines, alkoxyamines and alcohols include, for example, difunctionalized diamine ethylenes and alkenes, difunctionalized secondary ethylene and alkenes, difunctionalized aminooxy ethylenes and alkenes, combinations thereof, and the like.

In embodiments, the present disclosure provides for the synthesis of nanoparticle (NP) networks, sometimes referred to, in embodiments, as nanosponges, in a variety of sizes through the controlled crosslinking reaction of ketone groups integrated into linear polyester backbones and a difunctionalized aminooxy ethylene crosslinker. The resulting ketoxime linkages are pH responsive and provide an alternative, faster degradation mechanism together with hydrolysis of the polymer backbone. The reduction of the ketoxime linkages after nanoparticle formation results in nanoparticles of comparable sizes with stable alkoxyamine groups, limiting the degradation to a slower hydrolysis.

In this manner, nanoparticles and/or nanonetworks may be formed with different portions having different degradation rates: ketoxime linkages which are pH responsive and degrade quickly; and alkoxyamine linkages which hydrolyze more slowly and thus degrade more slowly. The difference in degradation rates will correspondingly affect the rate of release of a bioactive agent from the nanoparticles and/or nanonetworks, with a quicker rate of release of bioactive agent from a region possessing ketoxime linkages and a slower rate of release of bioactive agent from a region possessing alkoxyamine linkages.

While the instant disclosure discusses in detail a polymer backbone formed by copolymerization of 2-oxepane-1,5-dione (OPD) monomers together with δ-valerolactone, and then crosslinking the resulting polymer by reaction with a difunctionalized aminooxy ethylene crosslinker, it is to be appreciated that similar reaction chemistries may be used to form alternate copolymers and crosslinkng them with similar crosslinking agents.

For example, monomers such as alpha-methylene-gamma-butyrolactone (Tupaline A), alpha-methylene-gamma valerolactone, combinations thereof, and the like, may be reacted with other lactones. The resulting polymer, having reactive functional groups in the polymer backbone, may be similarly crosslinked with other crosslinking agents such as primary amines forming imine derivatives, secondary amines forming enamine derivatives, alkoxy amines forming oximes, alcohols forming acetals, combinations thereof, and the like. Exemplary amines, alkoxyamines and alcohols include, for example, difunctionalized diamine ethylenes and alkenes, difunctionalized secondary ethylene and alkenes, difunctionalized aminooxy ethylenes and alkenes, combinations thereof, and the like. Exemplary thiols include, for example, dithiol ethylenes and alkenes.

In other embodiments, alternate routes for incorporating crosslinking units into the backbone of a polymer chain may be used. For example, monomers such as itaconates, succinates, and/or fumarates, may be copolymerized using an ADMET copolymerization reaction. The chemical reaction responsible for ADMET polymerization is olefin metathesis catalyzed by metal alkylidenes. ADMET occurs via step polymerization of linear monomers. The key mechanistic features of ADMET are illustrated in Scheme 1 below.

reactive monomer unit (RMU) which is used, in embodiments in amounts from about 0.0027-0.006 mmol/ml.

The crosslinking agent and functionalized polymer may react at room temperature, or other suitable temperatures, in embodiments at a temperature from about 0° C. to about 120° C., in some embodiments from about 10° C. to about 100° C. in other embodiments from about 20° C. to about 90° C., to depending on the solvent.

The formation of nanoparticles may take place over a period of time from about 15 minutes to about 24 hours, in embodiments from about 30 minutes to about 18 hours, in other embodiments from about 1 hour.

The size of the resulting nanoparticles may be from about 20 nm to about 1400 nm, in embodiments from about 25 nm Scheme 1

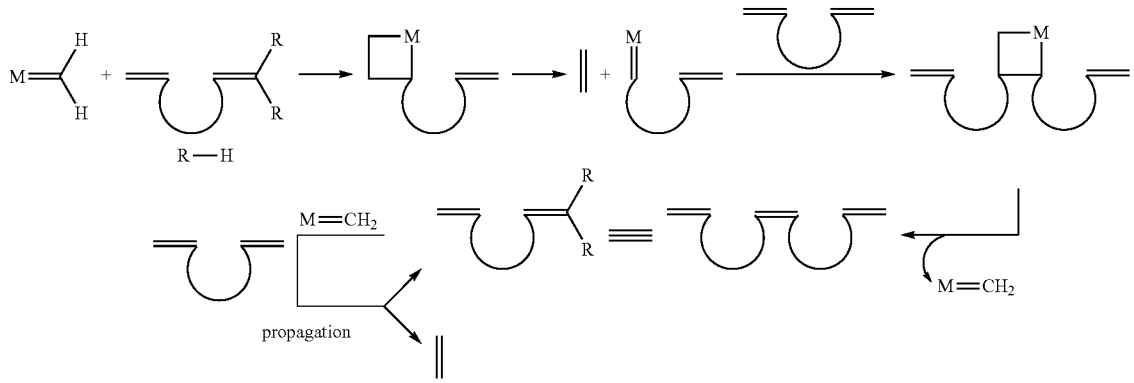

The resulting polymer includes units of some or all of the above-referenced monomers. Where present, the itaconate and/or fumarate in the resulting polymer backbone may be crosslinked using a suitable crosslinking agent, with the succinate used as a spacer unit in the polymer backbone.

Where the polymer backbone includes itaconates, fumarates, succinates, etc., suitable crosslinking agents include amines, primary amines, secondary amines, alkoxy amines, alcohols, thiols, combinations thereof, and the like. Exemplary amines, alkoxyamines and alcohols include, for example, difunctionalized diamine ethylenes and alkenes, difunctionalized secondary ethylene and alkenes, difunctionalized aminooxy ethylenes and alkenes, combinations thereof, and the like. Exemplary thiols include, for example, dithiol ethylenes and alkenes.

Once the polymer backbone with functional groups therein has been prepared, particles may then be formed in a one-step process starting from the different starting polymers with controlled crosslinking of the functional backbone of those polymers. The crosslinking agent may be combined with the functionalized polymer using any method within the purview of those skilled in the art. In embodiments, the crosslinking agent may be placed in a suitable solution which is then applied to the functionalized polymer. Methods for applying solutions include, for example, dipping, spraying, solution casting, ink jet printing, emulsion, suspension, combinations thereof, and the like.

Where applied as a solution, the crosslinking agent may be placed in a suitable solvent including, for example, dichloromethane, tetrahydrofurane, chloroform, and combinations thereof. The crosslinking agent may be combined with the solvent so that the reactive functional group, e.g., the amine, alkoxyamine, and/or thiol unit is in 1-10 eq to the to about 210 nm, in embodiments from about 35 nm to about 175 nm, other embodiments from about 39 nm to about 173 nm.

Continuing the crosslinking reaction between the polymeric backbones results in the continual formation of crosslinks, thereby connecting more polymeric backbones to form connected nanoparticles or nanonetworks, referred to, in embodiments, as nanosponges.

The resulting nanosponge may have a diameters from about 10 nm to about 1400 nm, in embodiments from about 100 nm to about 1200 nm, in other embodiments from about 200 nm to about 1000 nm.

The resulting particles may be useful as drug delivery systems as a practical synthesis is combined with a tunable degradation leading to expanded options for drug release.

For example, where the backbone possesses a ketoxime connective group, in some embodiments the ketoxime connective group may be further reduced. The ketoxime bond is a reversible cleavable bond and sensitive towards pH changes and makes these connectivities attractive for controlled disassembly to direct drug release. Moreover, the ketoxime bond can be converted into a stable non-reversible alkoxyamine bond through reduction, providing the option for tuning and postmodification.

As noted above, in some embodiments, the nanoparticles of the present disclosure may be combined with one or more bioactive agents for use a drug delivery device. The bioactive agent may be bound to the nanoparticles through chemical or ionic linkages, incorporated within a matrix of the nanoparticles, or both. For example, in some embodiments the bioactive agent may bind to a functional group within the polymer backbone or pendant thereto. In other embodiments, the drug is incorporated by entrappment in the polymer network and hydrogen bonding.

The term "bioactive agent", as used herein, is used in its broadest sense and includes any substance or mixture of substances that may have clinical use. Consequently, bioactive agents may or may not have pharmacological activity per se, e.g., a dye. Alternatively, a bioactive agent could be any agent which provides a therapeutic or prophylactic effect, a compound that affects or participates in tissue growth, cell growth or cell differentiation, a compound that may be able to invoke a biological action such as an immune response, or could play any other role in one or more biological processes.

Examples of classes of bioactive agents which may be utilized in accordance with the present disclosure include antimicrobials, antifungal, anticancer, antidiabetic, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, proteins, growth factors and enzymes. It is also intended that combinations of bioactive agents may be used in the present compositions.

Other bioactive agents which may be included as a bioactive agent in the compositions of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

In embodiments, suitable bioactive agents may include Brefeldin A, doxorubicin, atorvastatin, simvastatin, methotrexate, finasteride, camptothecin, taxol, photoactive compounds, dyes, fluorescent compounds, porphyrin based compounds, cis-platinum compounds, metallo-organic compounds, and combinations thereof.

A single bioactive agent may be utilized in the present compositions or, in alternate embodiments, any combination of bioactive agents may be utilized.

The bioactive agent may be present in the resulting nanosponge in an amount from about 1% by weight of the nanosponge to about 25% by weight of the nanosponge, in embodiments from about 5% by weight to about 20% by weight of the nanosponge, in other embodiments from about 7.5% by weight to about 17.5% by weight of the nanosponge.

For administration to a patient, in embodiments a mammal, the nanoparticles and bioactive agent may be placed into solution, with the solution being delivered to the patient.

In other embodiments, as noted above, the nanoparticles and bioactive agent form a nanosponge possessing the bioactive agent, which may then be implanted into the patient.

In yet other embodiments, the polymer possessing the functionalized backbone may be in one solution, optionally in combination with a bioactive agent, and the crosslinker may be in a second solution, optionally in combination with a bioactive agent. The two solutions may then be introduced in situ, whereby the polymer possessing the functionalized backbone reacts with the crosslinker to form the nanoparticles/nanosponges of the present disclosure. Where present, the resulting nanoparticles/nanosponges possess the bioactive agent.

Means for implanting the nanosponges and/or introducing multiple solutions, for example a dual syringe or similar device, are within the purview of a person of ordinary skill in the art.

Following the teachings of the present diclsosure, this practical synthesis of nanoparticles has demonstrated control over the nanoscopic dimension, crosslinking density, particle degradability, and controlled drug release engaging ketoxime and alkoxyamine linkage in nanonetworks containing polyesters and PEG units as constitutional elements.

The two different chemical connections thus generated result in two different release profiles designed to degrade faster in the tumor environment.

The methods of the present disclosure and the nanoparticles and nanonetworks thus produced are able to incorporate, release and deliver small molecule drugs, synthetic and natural drugs, in a postloading process. Depending on the nanonetwork density and degradability of the network, the release of these drugs can be tailored. One advantage of the disclosed nanoparticles and nanonetworks over other delivery system is the ability to adjust the polymer networks simply by the amount of crosslinker, concentration of the solution, and the crosslinking unit in the polymer backbone. Additionally, the system can be made more sophisticated with the conjugation of targeting units.

In general, the nanoparticles and nanonetworks of the present disclosure degrade in vivo over a period from about 1 day to about 16 weeks, in embodiments from about 10 days to about 12 weeks, in other embodiments from about 20 days to about 8 weeks. As noted above, in some embodiments, different bonds forming the nanoparticles may have different degradation rates. Thus, for example, where both fast degrading ketoxime bonds and slow degrading alkoxyamine bonds are both present in the same nanoparticles and/or nanonetworks, the resulting nanoparticles and/or nanonetworks may have multiple degradation rates. Thus, in some embodiments, the fast degrading bonds, in embodiments ketoxime bonds, may degrade in vivo over a period from about 1 day to about 4 weeks, in embodiments from about 2 days to about 2 weeks, in embodiments from about 3 days to about 1 week.

The nanoparticles and/or nanonetworks of the present disclosure may thus release a bioactive agent in vivo over a period of time from about 1 hour to about 3 weeks, in embodiments from about 8 hours to about 2 weeks, in embodiments from about 12 hours to about 1.5 weeks.

The present disclosure thus provides a practical approach for producing these materials while maintaining the ability to facilitate the release and delivery of small molecule hydrophobic drugs.

In addition, in some embodiments, the methods of the present disclosure may be further modified to include crosslinking of pendant functional groups so that the resulting nanoparticles and nanonetworks have crosslinking along both the polymer backbone as described above, but also include crosslinking of pendant functional groups in addition to the crosslinking along the polymer backbone. Methods for carrying out crosslinking with pendant functional groups include those disclosed in U.S. Pat. No. 9,856,348, the disclosure of which is hereby incorporated by reference in its entirety.

Advantages of the present disclosure, with respect to the particle design and the resultant properties of the nanoparticles and nanonetworks produced therefrom, include, but are not limited to:

The crosslinking unit of the linear polymer is part of the polymer backbone and need not include a pendant functional unit.

The synthesis can be more practical, as functional units do not have to be modified before crosslinking in contrast with previous strategies preparing pendant functional units.

The oxime crosslinking chemistry allows pH directed release kinetics, since oxime bonds are pH labile, i.e., they will degrade at a certain pH or range of pH. These oxime crosslinking bonds can be reduced to alkoxyamines, which are not pH labile, i.e., their degradation is not influenced by pH. Thus, the methods of the present disclosure produce particles with fully or partially reduced oxime groups. Accordingly, it is possible to tune the amount of oxime and alkoxyamine groups present within a particle, which permits the formation of particles having tuned release profiles of hydrophobic small molecule drugs therefrom.

Fully reduced alkoxyamine bonds are not pH labile and the nanoparticle degrades through a hydrolytic mechanism and the release profiles of drugs, dyes, proteins, peptides can be tuned by the crosslinking density of the nanosponges Nanoparticles prepared through aza-Michael or thiol Michael addition are degraded by hydrolysis and the release profiles of drugs, dyes, proteins, peptides can be tuned by the crosslinking density of the nanosponges.

Advantages when compared with other release systems include the fact that the methods of the present disclosure provide a practical synthesis method that is sensitive to release rates of drugs, size dimensions of particles, and postloading of the drug. Postloading can be done after the particle is made, so the drug can be incorporated much more efficiently compared with prior synthetic methods.

The following Examples are provided to illustrate, but not to limit, the features of the present disclosure so that those skilled in the art may be better able to practice the features of the disclosure described herein.

EXAMPLES

Materials. SiliaMetS® Cysteine was purchased from Silicycle. Spectra/Por® dialysis tubing (1 kD MWCO) and Float-a-Lyne® dialysis devices (1000 kD MWCO) were purchased from Spectrum Labs. SnakeSkin™ dialysis tubing (10 kD MWCO) was purchased from ThermoFisher Scientific. O,O'-(((oxybis(ethane-2,1-diyl))bis(oxy))bis(ethane-2,1-diyl))bis(hydroxylamine), also referred to as bis(aminooxy)-PEG3, was purchased from Broadpharm. 1,4-cyclohexanedione was purchased from Tokyo Chemical Industry America. Carbon grids for electron transmission microscopy (TEM) were purchase from TED PELLA. Bis-PEG5-thiol, was purchased from Broadpharm. Deuterated chloroform was purchased from Cambridge Isotope Laboratories. All other reagents and solvents were purchased from Sigma-Aldrich and used without further purification unless otherwise noted. δ-Valerolactone was purified via vacuum distillation prior to polymerization.

Characterization. $^1$H and $^{13}$C NMR spectra were recorded on Bruker AV-I 400, JEOL ECX-400, and JEOL ECA-600 II spectrometers. Chemical shifts were referenced to solvent resonance signals. Gel permeation chromatography (GPC) was conducted on a ToSOH EcoSEC HLC-8320GPC system equipped with a refractive index detector, UV-8320 detector, and TSKgel HHR columns (7.8×300 mm G5000HHR, G4000HHR, and G3000HHR) with tetrahydrofuran (THF) as the eluent at a flow rate of 1 mL/min. Transmission Electron Microscopy (TEM) was performed using an JEOL 2000-FX microscope operated at 200 kV. Some samples for transmission electron microscopy (TEM) were prepared by dissolving nanoparticles (~0.5 mg) in 0.22 μm filtered acetonitrile (ACN). Other samples for TEM were prepared by dissolving approximately 1.5 mg of particles in 2:1 isopropyl alcohol (IPA): acetonitrile (ACN). The samples were then stained with 3 drops of 3% phosphotungstic acid monohydrate and vortexed. Carbon grids were prepared by dipping an Ultrathin Carbon Type-A 400 Mesh Copper Grid in the sample solution three times and allowing to dry at ambient temperature for 12 hours. Dynamic light scattering (DLS) was performed on a Malvern Zetasizer Nano system with a fixed angle of 173° at 25° C. All particles were measured in 0.22 μm filtered THF diluted to a concentration that produced the desired count rate with a low signal-to-noise ratio. Static light scattering was performed using the Molecular Weight function of a Malvern Zetasizer Nano system in THF between 0.01-0.1 mg/mL concentrations. High performance liquid chromatography (HPLC) analysis of drug concentration was conducted using a ThermoFisher Ultimate 3000 HPLC system and Phenomenex column (Luna 5 μ C8(2) 100 Å, 150×4.6 mm, 5 μm) with an isocratic mixture of methanol and water (57:43) and flow rate of 1.0 mL/min at 230 nm.

Example 1

Synthesis of 2-oxepane-1,5-dione. The procedure was modified from the literature, particularly the procedure described in Jean-Pierre Latere, P. L., Philippe Dubois, Robert Jerome, 2-Oxepane-1,5-dione: A Precursor of a Novel Class of Versatile Semicrystalline Biodegradable (Co)polyesters. Macromolecules 2002, 35 (21), 7857-7859.

Meta-chloroperoxybenzoic acid (11.99 grams, 54 mmol) and 1,4-cyclohexanedione (4.0 grams, 36 mmol) was dissolved in anhydrous dichloromethane (DCM) (45.5 mL) and refluxed for 3 hours. The reaction mixture was cooled to room temperature and a white precipitate was removed by gravity filtration. The precipitate was washed with excess DCM (10 mL) to solubilize any residual product. The organic layer was dried over anhydrous magnesium sulfate and dried in vacuo to collect a white solid. Diethyl ether (10 mL) was added to the flask to wash and collect a white solid via vacuum filtration (80% yield). Results of $^1$H NMR (400 MHz, CDCl$_3$): δ 2.70-2.73 (m, 2H); 2.81-2.85 (m, 4H); 4.42 (t, 2H) $^{13}$C NMR (600 MHz, CDCl$_3$): δ 27.8, 38.5, 44.6, 63.3, 173.5, 205.1.

Example 2

General synthesis of poly(δ-valerolactone-2-oxepane-1,5-dione) (P(VL-co-OPD)). Tin(II) trifluoromethanesulfonate (3.93 mg, 9.25×10−3 mmol), isoamyl alcohol (81.72 μL, 7.5×10−1 mmol), and DCM (2.61 mL) were added to a flame dried and N2 purged flask. δ-valerolactone (VL, 2.57 mL, 27 mmol) and 2-oxepane-1,5-dione (OPD, 0.22 grams, 1.8 mmol) were added at 0° C. then stirred at room temperature for 18 hours. The reaction mixture was quenched with excess methanol (3 mL) and a solid-support metal scavenger (SiliaMetS® Cysteine, 150 mg) was added and stirred for 2 hours to capture tin catalyst. The mixture was filtered via gravity filtration and transferred to dialysis tubing (1 kD MWCO) and dialyzed against methanol (MeOH)/DCM (1:1) mixture for 24 hours, with frequent solvent changes. After dialysis, the solvent was removed under reduced pressure and product dried in vacuo to obtain a light yellow, waxy product. (56% yield) $^1$H NMR (400 MHz, CDCl$_3$): δ 0.90 (d, 6H); 1.6-1.75 (m); 2.23-2.43 (m); 2.25-2.7 (m); 2.7-2.84 (m); 3.4 (t); 3.65 (m); 4.0 (t); 4.3-4.4 (m). (See, FIG. 1.) $^{13}$C NMR (600 MHz, CDCl$_3$): δ 21.25, 27.9, 33.5, 63.8, 173.2, 205.75.

Example 3

Figure 2:
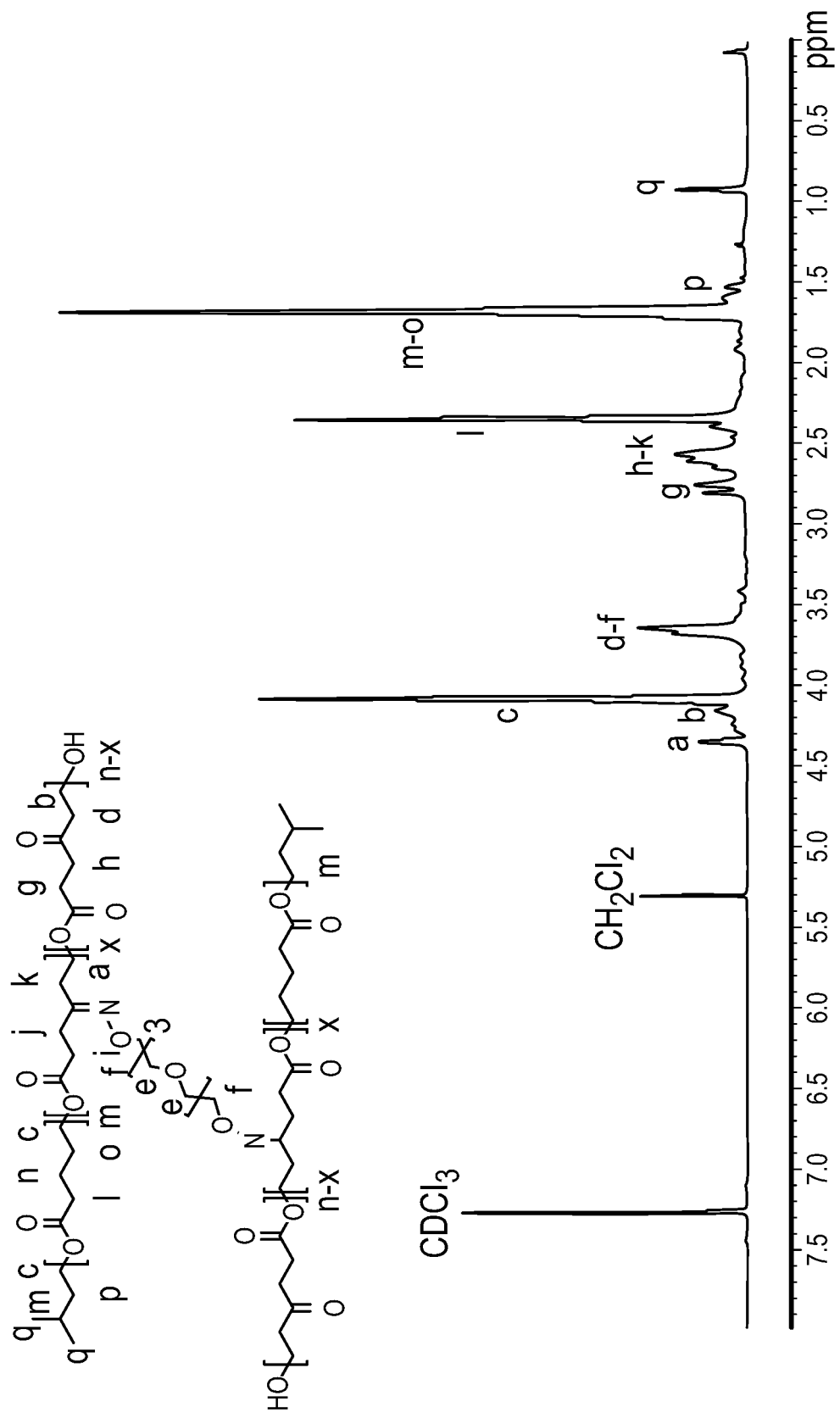
FIG. 2 is a 400 MHz $^1$H NMR characterization of ketoxime nanoparticles in $CDCl_3$.

General synthesis of ketoxime nanoparticle (NPKO). P(VL-co-OPD) (4% OPD, 50 mg, 4556.20 grams mol-1, 2925.14 grams mol-1 keto-group, 1.71×10−5 mol) was dissolved in dichloromethane (5.70 mL) then added to a 50 mL round bottom flask. O,O'-(((oxybis(ethane-2,1-diyl))bis(oxy))bis(ethane-2,1-diyl))bis(hydroxylamine) (3.83 mg, 1.71×10−5 mol, 1 equiv.) was dissolved in dichloromethane (0.63 mL) and added quickly to the polymer solution at a fast vortex. The reaction was stirred for 2 hours then immediately transferred to Thermo Scientific™ SnakeSkin™ 10K MWCO Dialysis Tubing. The solution was dialyzed against dichloromethane for 48 hours, changing the solvent 3-4 times per day. The solvent was removed via rotary evaporation. The product was dried in vacuo to yield a light tan waxy solid (80% yield). $^1$H NMR (400 MHz, CDCl$_3$): δ 0.90 (d, 6H); 1.6-1.75 (m); 2.23-2.43 (m); 2.25-2.7 (m); 2.7-2.84 (m); 3.4 (t); 3.65 (m); 4.0 (t); 4.3-4.4 (m). (See, FIG. 2.) $^{13}$C NMR (600 MHz, CDCl$_3$): δ 21.32, 25.53, 28.00, 33.62, 63.87, 67.98, 173.30.

Example 4

General Synthesis of Partially Reduced Ketoxime/Alkoxyamine Nanoparticle (NPKO/AA). To ketoxime nanoparticles (348 mg) formed in situ, sodium cyanoborohydride (6.72 mg, 1.07×10−4 mol, 0.5 equiv.) and a catalytic amount of saturated sodium bicarbonate solution (100 μL) were added directly to the reaction flask. The reaction stirred for 2 hours then was transferred to Thermo Scientific™ SnakeSkin™ 10K MWCO Dialysis Tubing. The solution was dialyzed against a 1:1 mixture of MeOH/DCM for 48 hours, with 3-4 solvent changes per day. The solution was filtered with a 0.45 μm filter to remove solid salt particulates and solvent was removed via rotary evaporation. The product was dried in vacuo to yield a light tan waxy solid (80% yield). $^1$H NMR (400 MHz, CDCl$_3$): δ 0.90 (d, 6H); 1.6-1.75 (m); 2.23-2.43 (m); 2.25-2.7 (m); 2.7-2.84 (m); 3.4 (t); 3.65 (m); 4.0 (t); 4.3-4.4 (m). $^{13}$C NMR (600 MHz, CDCl$_3$): δ 21.32, 25.53, 28.00, 33.62, 63.85, 67.88, 173.26.

Example 5

Figure 3:
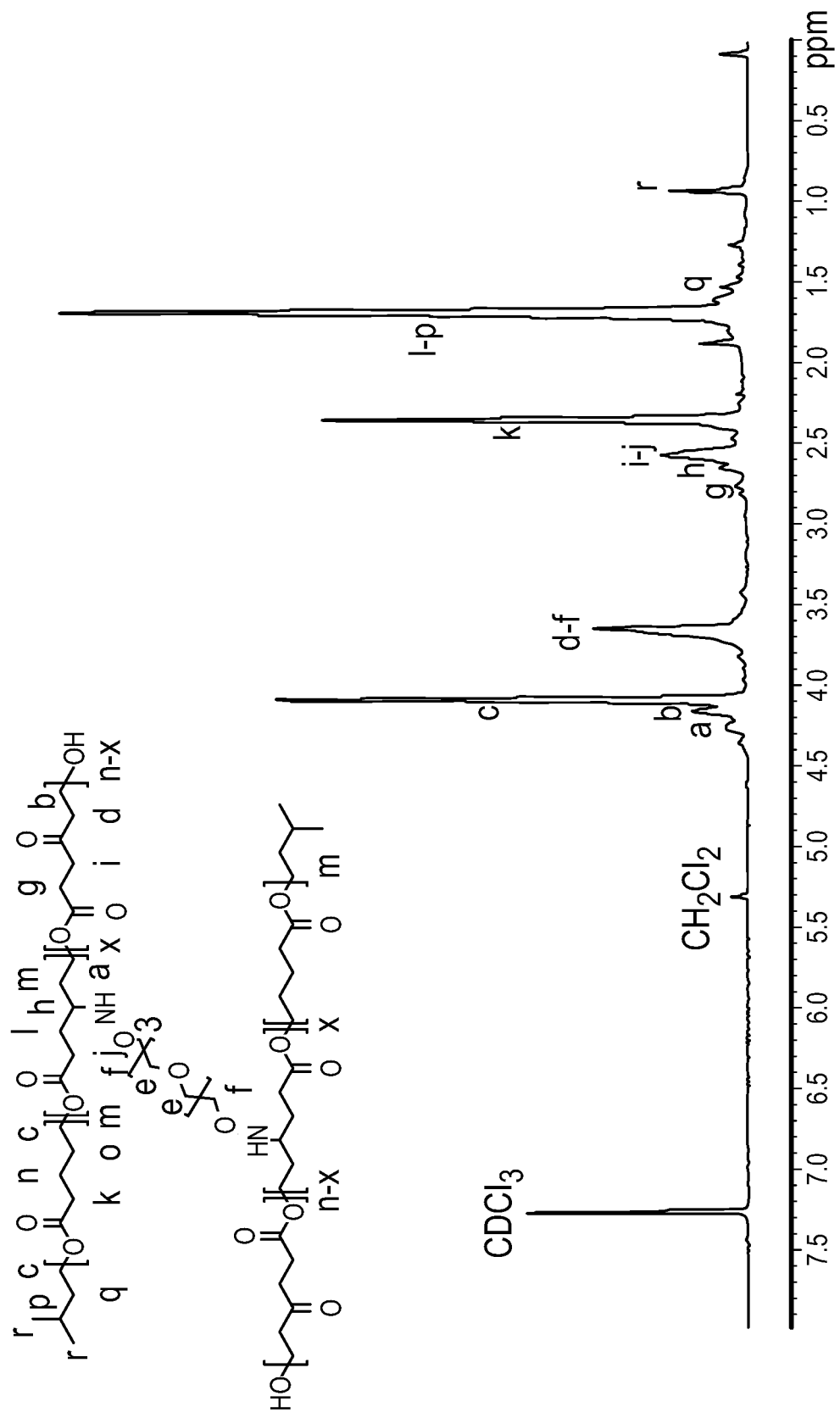
FIG. 3 is a 400 MHz $^1$H NMR characterization of alkoxyamine nanoparticles in CDCl$_3$.

General synthesis of alkoxyamine nanoparticle (NPAA). To ketoxime nanoparticles (50 mg) formed in situ, sodium cyanoborohydride (2.15 mg, 3.42×10−5 mol, 2 equiv.) and a catalytic amount of saturated sodium bicarbonate solution (100 μL) were added directly to the reaction flask. The reaction stirred for 2 hours then was transferred to Thermo Scientific™ SnakeSkin™ 10K MWCO Dialysis Tubing. The solution was dialyzed against a 1:1 mixture of MeOH/DCM for 48 hours, with 3-4 solvent changes per day. The solution was filtered with a 0.45 μm filter to remove solid salt particulates and solvent was removed via rotary evaporation. The product was dried in vacuo to yield a light tan waxy solid (80% yield). $^1$H NMR (400 MHz, CDCl$_3$): δ 0.90 (d, 6H); 1.6-1.75 (m); 2.23-2.43 (m); 2.25-2.7 (m); 2.7-2.84 (m); 3.4 (t); 3.65 (m); 4.0 (t); 4.3-4.4 (m). (See, FIG. 3.) $^{13}$C NMR (600 MHz, CDCl$_3$): δ 21.32, 25.53, 28.00, 33.62, 63.85, 67.88, 173.26.

Example 6

Figure 4:
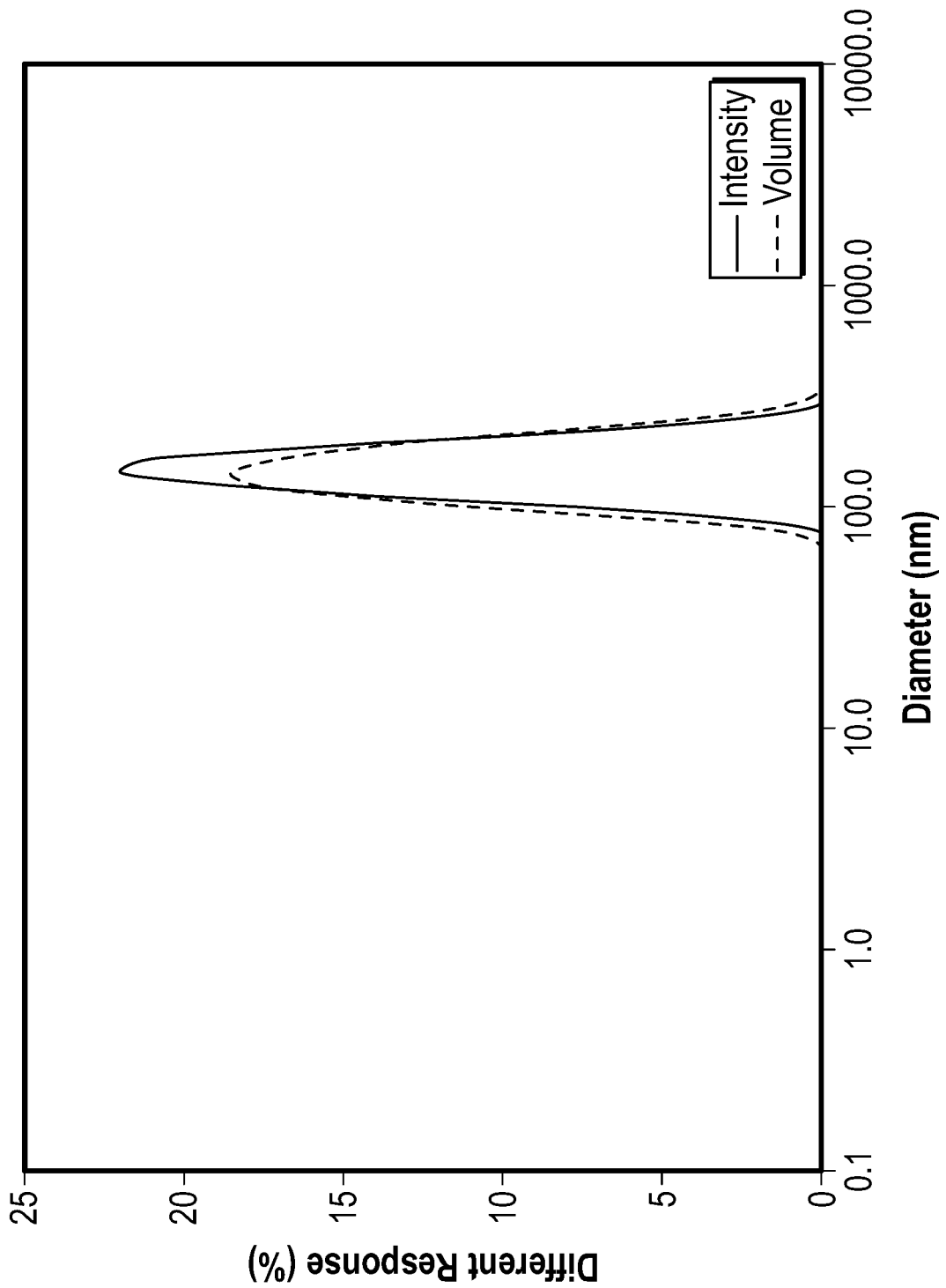
FIG. 4 is a graph depicting representative dynamic light scattering data of nanoparticles of the present disclosure measuring ~165 nm.

In vitro nanoparticle degradation studies. Successful formation of discrete nanoparticles was confirmed via transmission electron microscopy (TEM) and dynamic light scattering (DLS) (FIG. 4). NPs (14% OPD, 5.4 mM, ~170 nm) were suspended in 2 mL of 0.1M acetic acid-NaOAc buffer with 0.1% v/v Tween® 80 (pH 5.0) or phosphate buffered saline with 0.1% v/v Tween® 80 (PBS, pH 7.4) in 1 dram vials with a micro stir bar. The vials were sealed and samples were continuously stirred at 37° C. At 48 hours intervals, nanoparticles and degradation products were extracted with dichloromethane (3×3 mL). The organic layer was dried over magnesium sulfate and dried in vacuo. The degradation of particles was monitored via static light scattering utilizing the Molecular Weight function of a Malvern Zetasizer Nano instrument.

Example 7

Figure 5:
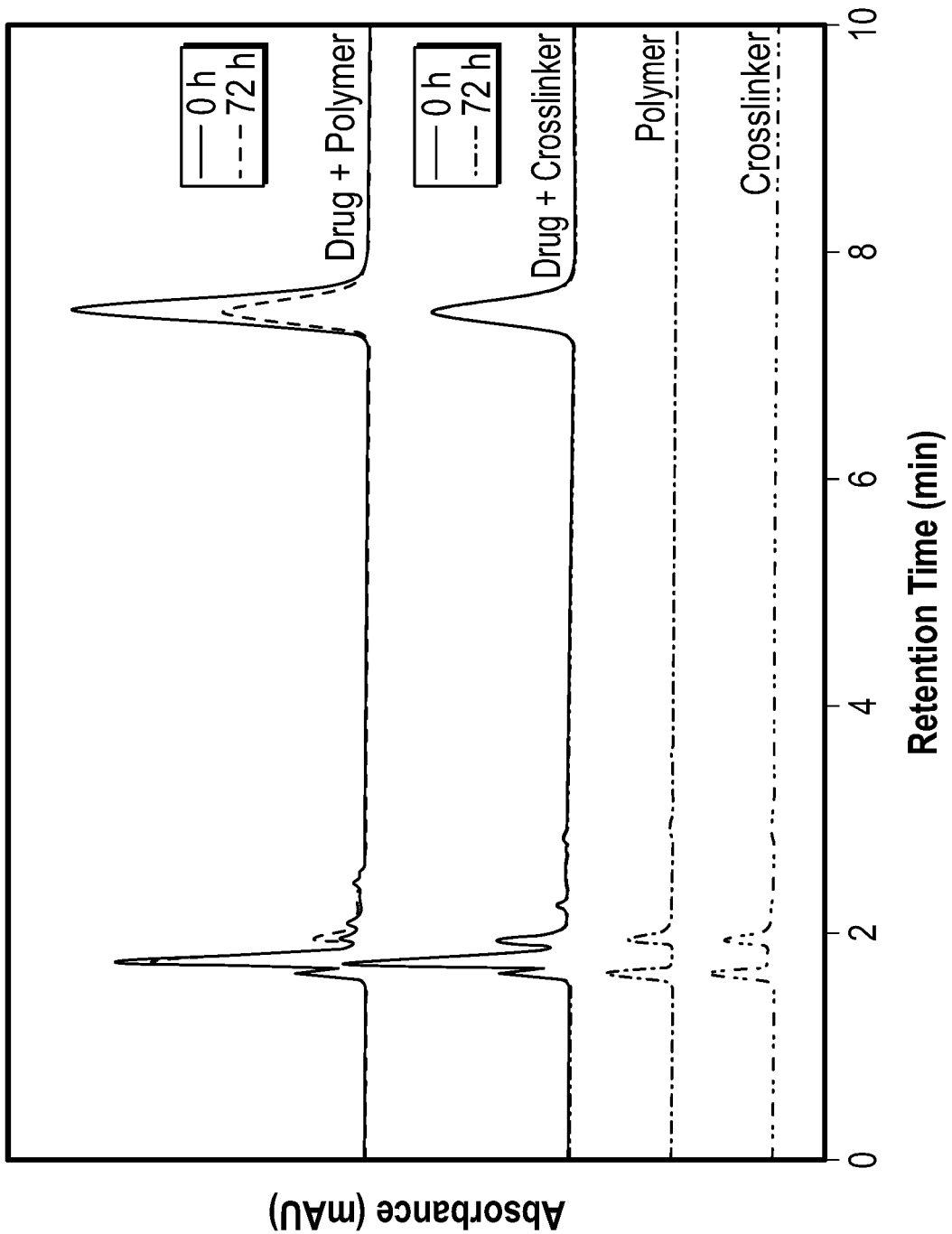
FIG. 5 is a graph depicting results of HPLC analysis of control experiment with physical mixture of drug (BFA) and polymer (P(VL-co-OPD)) or crosslinker (bis(aminooxy) PEG-3) in pH 5.0 at 0 and 72 hours post reaction.
Figure 6:
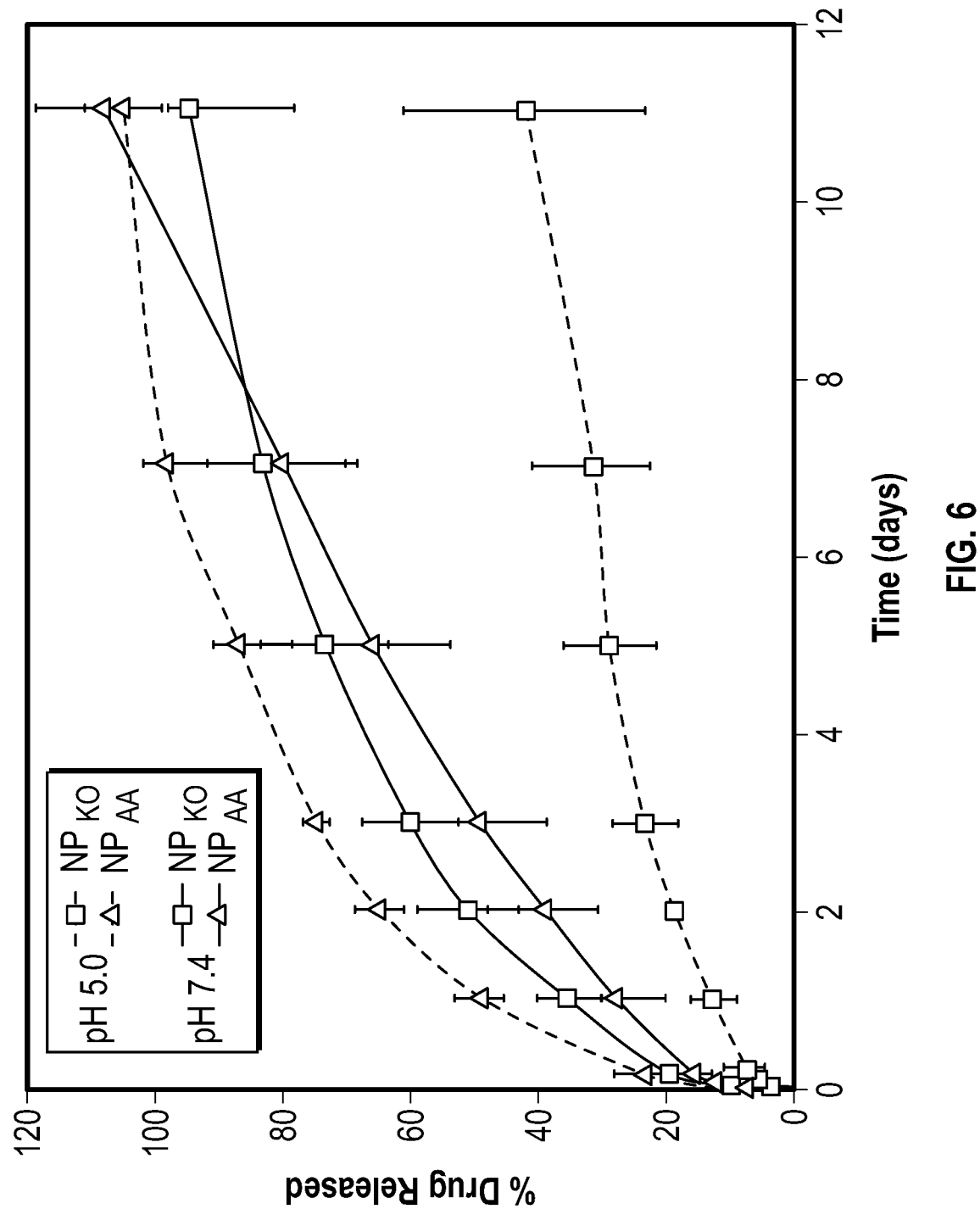
FIG. 6 is a graph depicting release of BFA from 8% OPD, 2.7 mM NP$_{KO}$ and NP$_{AA}$ in pH 5.0 and pH 7.4 at 37° C. over 11 days.

General Nanoprecipitation Procedure for Encapsulation of Brefeldin A into Nanoparticles. NPs (12.6 mg, 8% OPD, 2.7 mM, ~80 nm) were added to a 1.5 mL centrifuge tube. Brefeldin A (BFA) was solubilized in dimethyl sulfoxide (DMSO) to a known concentration and then added to the NPs (3.15 mg, 11.2 mmol). Additional DMSO was added to the mixture up to a total of 50 μL. Cell culture grade water containing 0.1% D-α-tocopherol polyethylene glycol 1000 succinate (1 mL) was added to the centrifuge tube and vortexed to induce BFA encapsulation. The mixture was then centrifuged at 14000 revolutions per minute (RPM) for 20 minutes. The supernatant was decanted, fresh cell culture grade water (1 mL) was added to the particle pellet and vortexed until particles were resuspended. Centrifugation was repeated at 14000 RPM for 20 minutes, then the supernatant was decanted to remove any unincorporated drug. Cell culture grade water (0.5 mL) was added to the mixture, frozen, and lyophilized to produce BFA encapsulated nanoparticles (BFA-NP). HPLC analysis confirmed encapsulation of BFA at an average of 19.9 wt % with 99.7% efficiency. (See, FIG. 5.)

Control Experiments for Particle-Drug Interaction of Brefeldin A and Ketoxime Nanoparticles. Brefeldin A (0.2 mg, 0.71 mmol) was added to a 1 dram vial containing either O,O'-(((oxybis(ethane-2,1-diyl))bis(oxy))bis(ethane-2,1-diyl))bis(hydroxylamine) (0.1 mg, 0.45 mmol) or P(VL-co-OPD) (8% OPD, 0.7 mg, 0.16 mmol) and mixed with minimal DMSO (20 μL). The mixture was diluted in 0.1M acetic acid-NaOAc buffer with 0.1% v/v Tween® 80 (pH 5.0, 1.5 mL) and stirred at 37° C. for 24 hours. The resulting mixture was analyzed at 0 and 72 hours post reaction via HPLC at 230 nm to evaluate any particle-drug interactions (See, FIG. 5).

Example 8

In vitro release of Brefeldin A from nanoparticles. BFA-NPs (~8 mg, ~20 wt % BFA) were weighed into a 1.5 mL centrifuge tube and 1 mL 0.1M acetic acid-NaOAc buffer with 0.1% v/v Tween® 80 (pH 5.0) or phosphate buffered saline with 0.1% v/v Tween® 80 (PBS, pH 7.4) was added. The mixture was vortexed until the particles were suspended in the media, and then the particles were transferred to a 1000 kD Float-a-Lyzer™ dialysis membrane. The dialysis device was placed in a 50 mL centrifuge tube containing 18 mL of dialysis media and a small stir bar. The centrifuge tube was submerged in a water bath at 37° C. and stirred, and aliquots (150 μL) were removed from the dialysis media at specified time points and replaced with fresh media. BFA concentration in the aliquots was determined via HPLC at 230 nm with isocratic gradient of 57% MeOH: 43% water. Flow rate of 1 mL/min with run time of 10 minutes yielded a retention time of 7.5 minutes.

General Nanoprecipitation Procedure for Encapsulation of Brefeldin A into NPKO/AA. NPs (134 mg, 8% OPD, 2.7 mM, ~80 nm) were added to a 1.5 mL centrifuge tube. Brefeldin A (BFA) was solubilized in dimethyl sulfoxide (DMSO) to a known concentration and then added to the NPs (35.2 mg, 125 mmol). Additional DMSO was added to the mixture up to a total of 300 μL. The solution was dispersed equally into seven 1.5 mL centrifuge tubes. Cell culture grade water containing 0.1% D-α-tocopherol polyethylene glycol 1000 succinate (1 mL) was added to each centrifuge tube and vortexed to induce BFA encapsulation. The suspension was then centrifuged at 14000 RPM for 20 minutes. The supernatant was decanted, fresh cell culture grade water (1 mL) was added to the particle pellet and vortexed until particles were resuspended. Centrifugation was repeated at 14000 RPM for 20 minutes, then the supernatant was decanted to remove any unincorporated drug. Cell culture grade water (0.5 mL) was added to the mixture, frozen, and lyophilized to produce BFA encapsulated nanoparticles (BFA-NP). HPLC analysis confirmed encapsulation of BFA at an average of 42 wt % with 210% efficiency. (See, FIG. 6.)

Example 9

In vitro release of Brefeldin A from NPKO/AA. BFA-NPs (~5 mg, ~40 wt % BFA) were weighed into a 1.5 mL centrifuge tube and 1 mL 0.1M acetic acid-NaOAc buffer with 0.1% v/v Tween® 80 (pH 5.0) or phosphate buffered saline with 0.1% v/v Tween® 80 (PBS, pH 7.4) was added. The mixture was vortexed until the particles were suspended in the media, and then the particles were transferred to a 1000 kD Float-a-Lyzer™ dialysis membrane. The dialysis device was placed in a 50 mL centrifuge tube containing 18 mL of dialysis media and a small stir bar. The centrifuge tube was submerged in a water bath at 37° C. and stirred, and aliquots (150 μL) were removed from the dialysis media at specified time points and replaced with fresh media. BFA concentration in the aliquots was determined via HPLC at 230 nm with isocratic gradient of 57% MeOH: 43% water. Flow rate of 1 mL/min with run time of 10 minutes yielded a retention time of 7.5 minutes.

Example 10

General synthesis of ketoxime nanoparticle (NPKO). P(VL-co-OPD) (14% OPD, 50 mg, 5514 grams/mol, 421.12 grams/mol keto-group, 0.119 mmol) was dissolved in dichloromethane (2 mL) then added to a 50 mL round bottom flask with the remaining DCM to yield desired final concentration (mmol keto-group to mL DCM). O,O'-(((oxybis(ethane-2,1-diyl))bis(oxy))bis(ethane2,1-diyl))bis (hydroxylamine) (5 or 10 equiv.) was dissolved in dichloromethane (2 mL) and added quickly to the polymer solution at a fast vortex. The reaction was stirred for 2 hours then immediately transferred to Thermo Scientific™ SnakeSkin™ 10K MWCO Dialysis Tubing. The solution was dialyzed against dichloromethane for 48 hours, changing the solvent 3-4 times per day. The solvent was removed via rotary evaporation. The product was dried in vacuo to yield a light tan waxy solid (85% yield).

Example 11

Monitoring the synthesis of ketoxime nanoparticle (NPKO). P(VL-co-OPD) (14% OPD, 50 mg, 5514 grams/mol, 421.12 grams/mol keto-group, 0.119 mmol) was dissolved in dichloromethane (2 mL) then added to a 50 mL round bottom flask with the remaining DCM to yield desired final concentration (mmol keto-group to mL DCM). O,O'-(((oxybis(ethane-2,1-diyl))bis(oxy))bis(ethane2,1-diyl))bis (hydroxylamine) (5 or 10 equiv.) was dissolved in dichloromethane (2 mL) and added quickly to the polymer solution at a fast vortex. The reaction was monitored by 1H NMR by taking 100 μL aliquots of the reaction mixture dissolved in CDCl3 every 30 minutes over a 4 hour timeperiod. No change in NMR was noticed after each timepoint. After 4 hours the reaction mixture was immediately transferred to Thermo Scientific™ SnakeSkin™ 10K MWCO Dialysis Tubing. The solution was dialyzed against dichloromethane for 48 hours, changing the solvent 3-4 times per day. The solvent was removed via rotary evaporation. The product was dried in vacuo to yield a light tan waxy solid (85% yield).

As is apparent from the above disclosure, particles of the present disclosure may be prepared by starting with the synthesis of poly(δ-valerolactone-co-2-oxepane-1,5-dione) (P(VL-co-OPD)) via ring-opening polymerization catalyzed by $Sn(OTf)_2$. OPD was chosen for the ability to directly copolymerize a ketone-bearing unit into the backbone, affording a one-step polymer precursor preparation. In embodiments, the present disclosure provides OPD incorporation of 4-20 mol % with monomer conversion ranging 47-63% (Table 1 below) for all polymers. The monomer feed ratio was varied (6-30 mol %) with a molecular weight target of 4000 $gmol^{-1}$ to investigate the control provided by increasing the amount of crosslinking functionality throughout the polymer backbone.

TABLE 1

GPC and NMR analysis of P(VL-co-OPD).

| Monomer Feed Ratio (VL:OPD) | % OPD$_{th}$ | % OPD$^a$ | OPD conv (%) | Polymer Composition (VL:OPD) | M$_{a\ theo}$ (g/mol) | M$_a^a$ (g/mol) | M$_a^b$ (g/mol) | M$_w^b$ (g/mol) | M$_w$/M$_n^b$ (g/mol) |
|---|---|---|---|---|---|---|---|---|---|
| 94:6 | 6 | 3.76 | 63 | 96:4 | 4000 | 4588 | 3000 | 4000 | 1.31 |
| 85:15 | 15 | 7.52 | 50 | 92:8 | 4000 | 4420 | 2800 | 3900 | 1.39 |
| 70:30 | 30 | 14.18 | 47 | 86:14 | 4000 | 3637 | 2800 | 3600 | 1.31 |

$^a$% OPD and Mn determined by 400 MHz 1H NMR in CDCl3.
$^b$Molecular weight and polydispersity measured by GPC at 40° C. in THF and a flow rate of 1 mL/min using using ToSOH EcoSEC HLC-8320GPC system equipped with a refractive index detector, UV-8320 detector, and TSKgel HHR columns (7.8 × 300 mm G5000HHR, G4000HHR, and G3000HHR).

Figure 7:
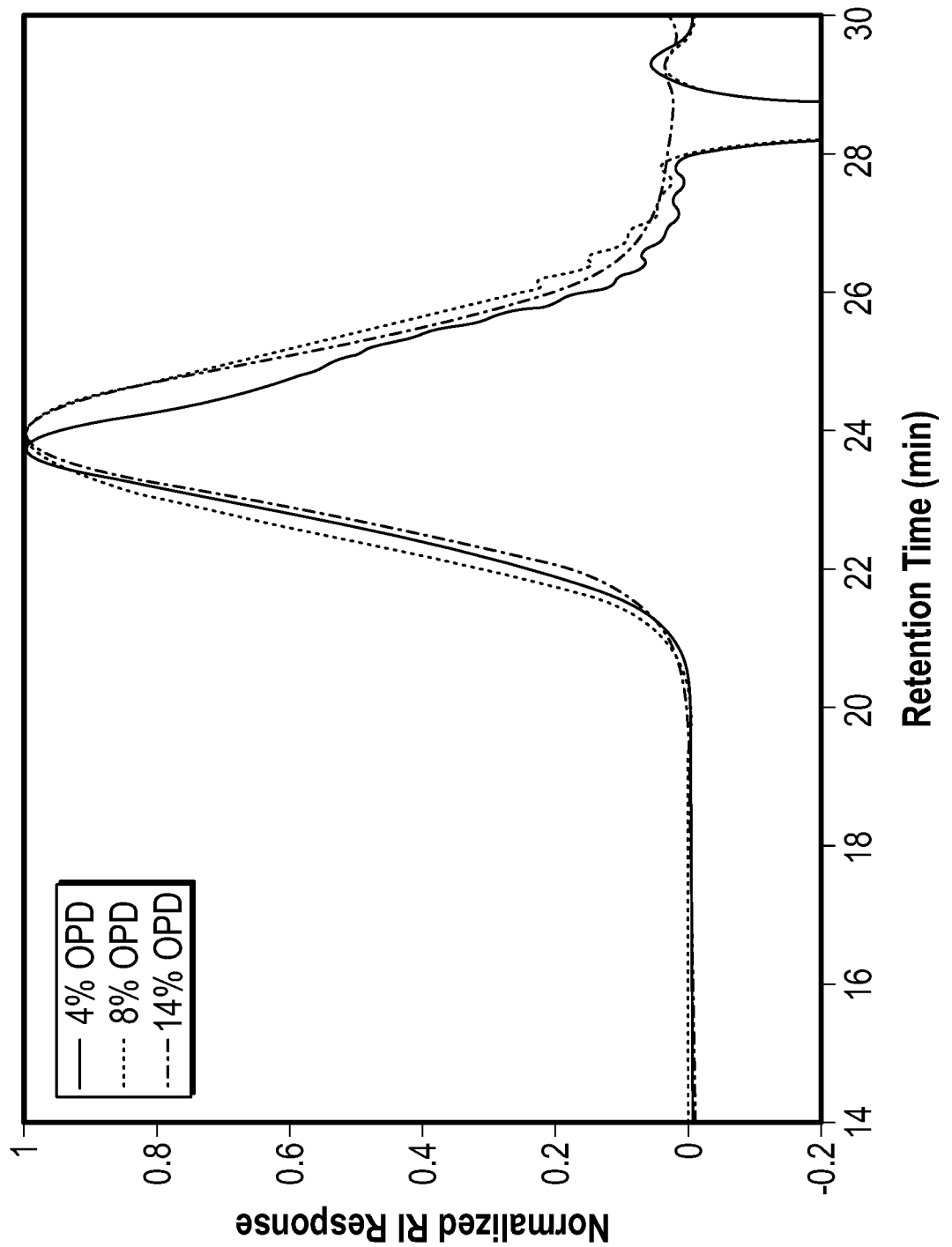
FIG. 7 is a graph depicting GPC traces of P(VL-co-OPD) at varying comonomer ratios, measured in tetrahydrofuran (THF) at 40° C. with a flow rate of 1 mL/min.
Figure 15:
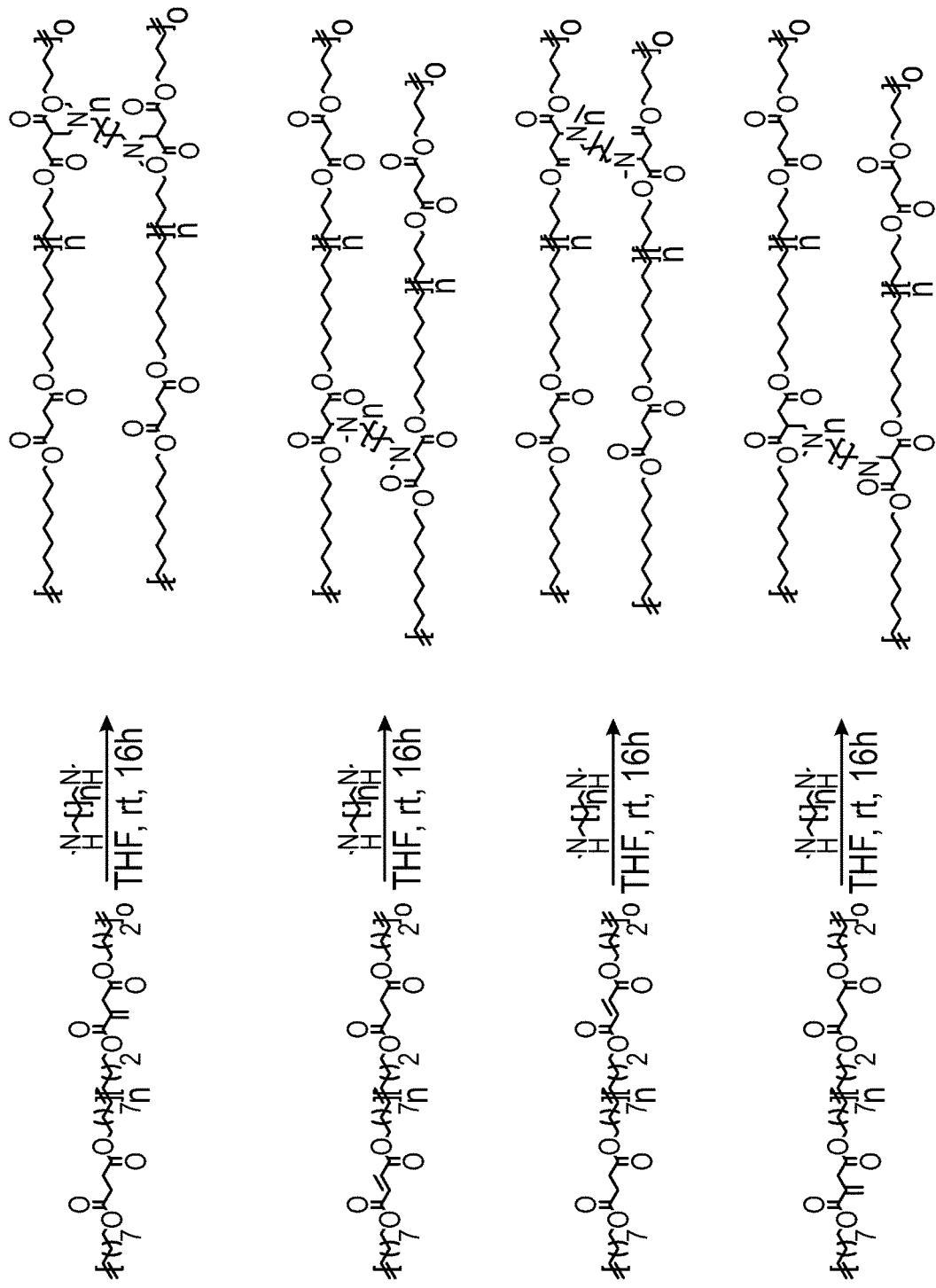
FIGS. 15-19 are representative summaries of aza-Michael addition particle formation reactions.
Figure 16:
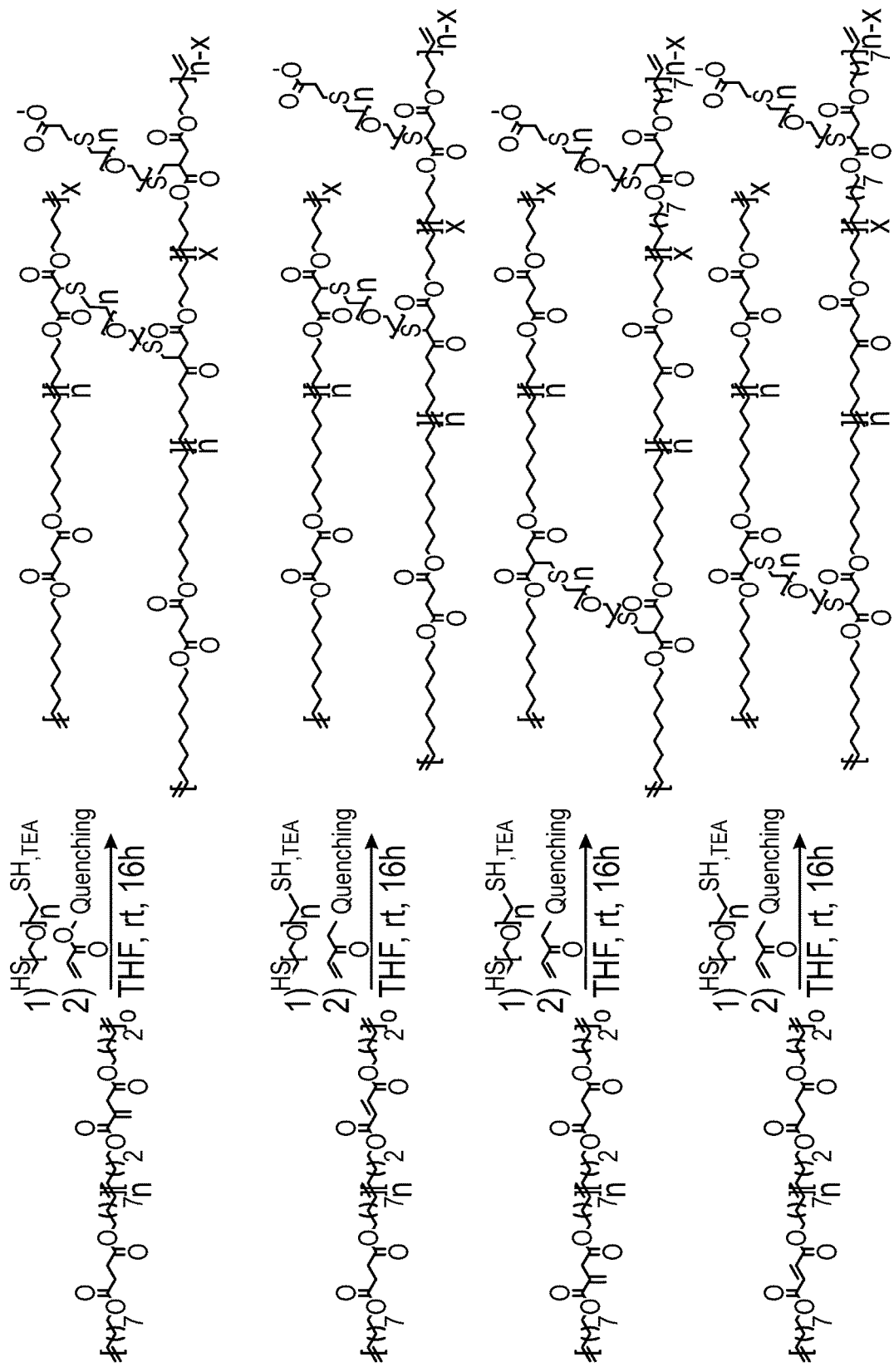
Figure 17:
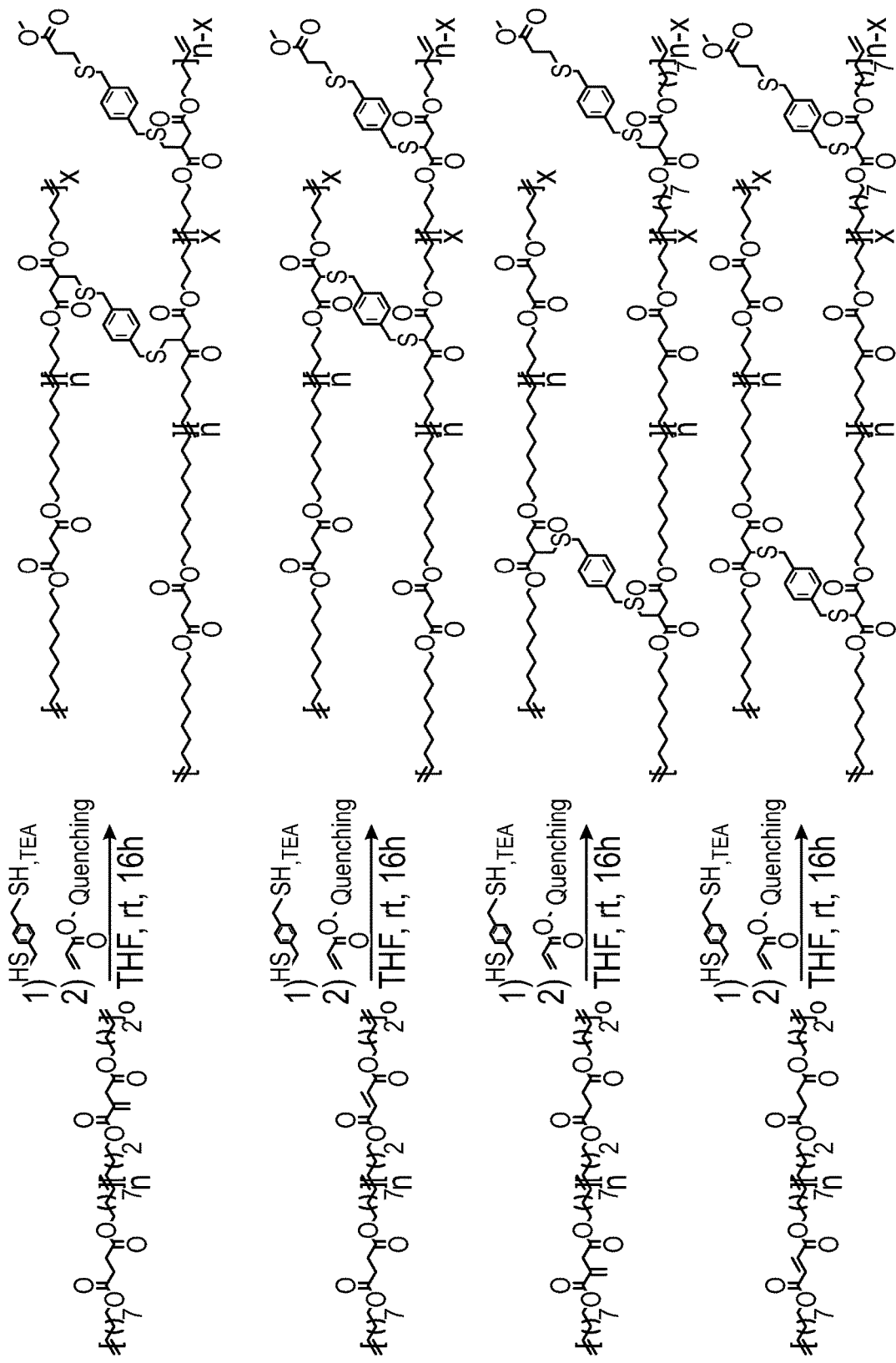
Figure 18:
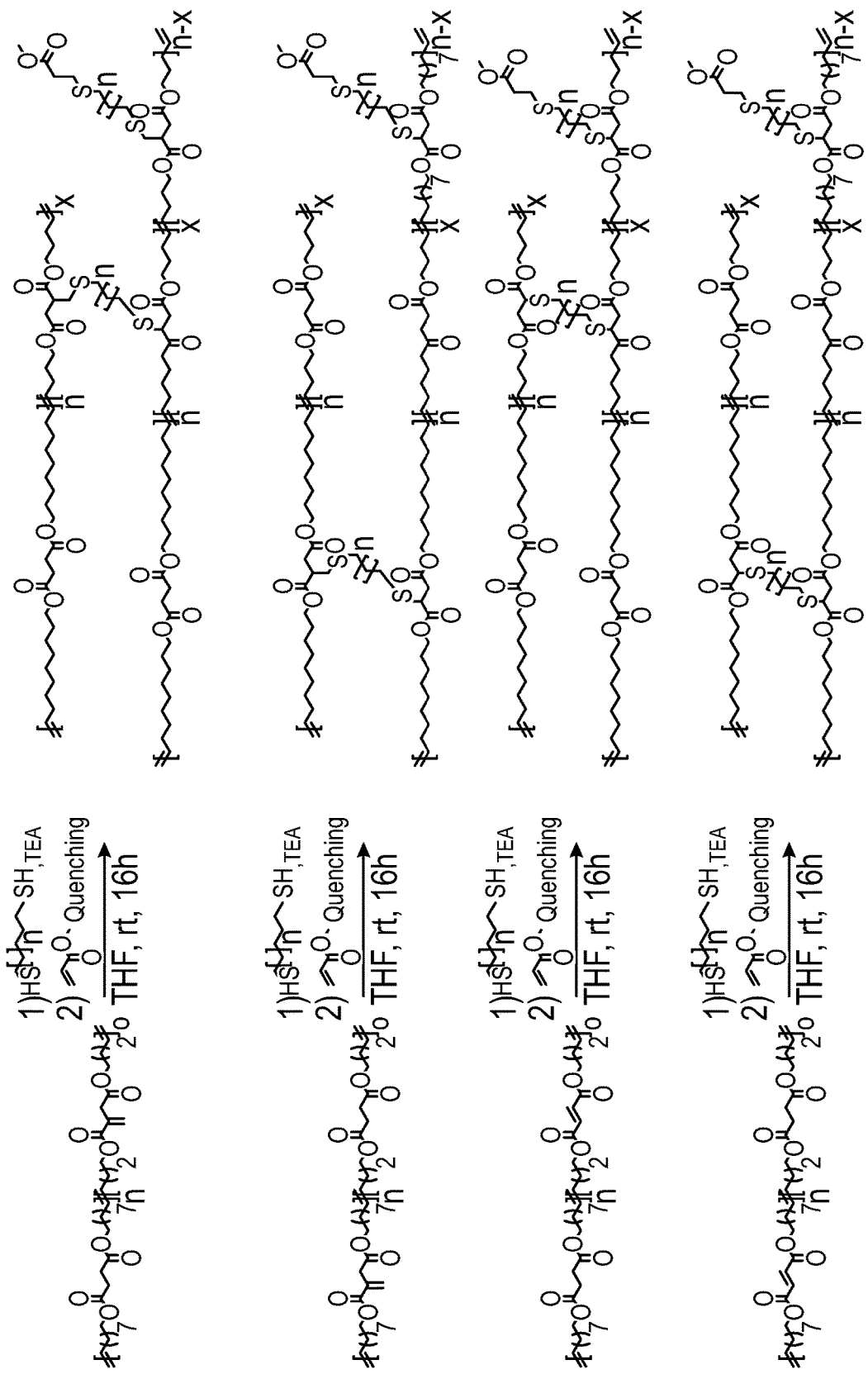
Figure 19:
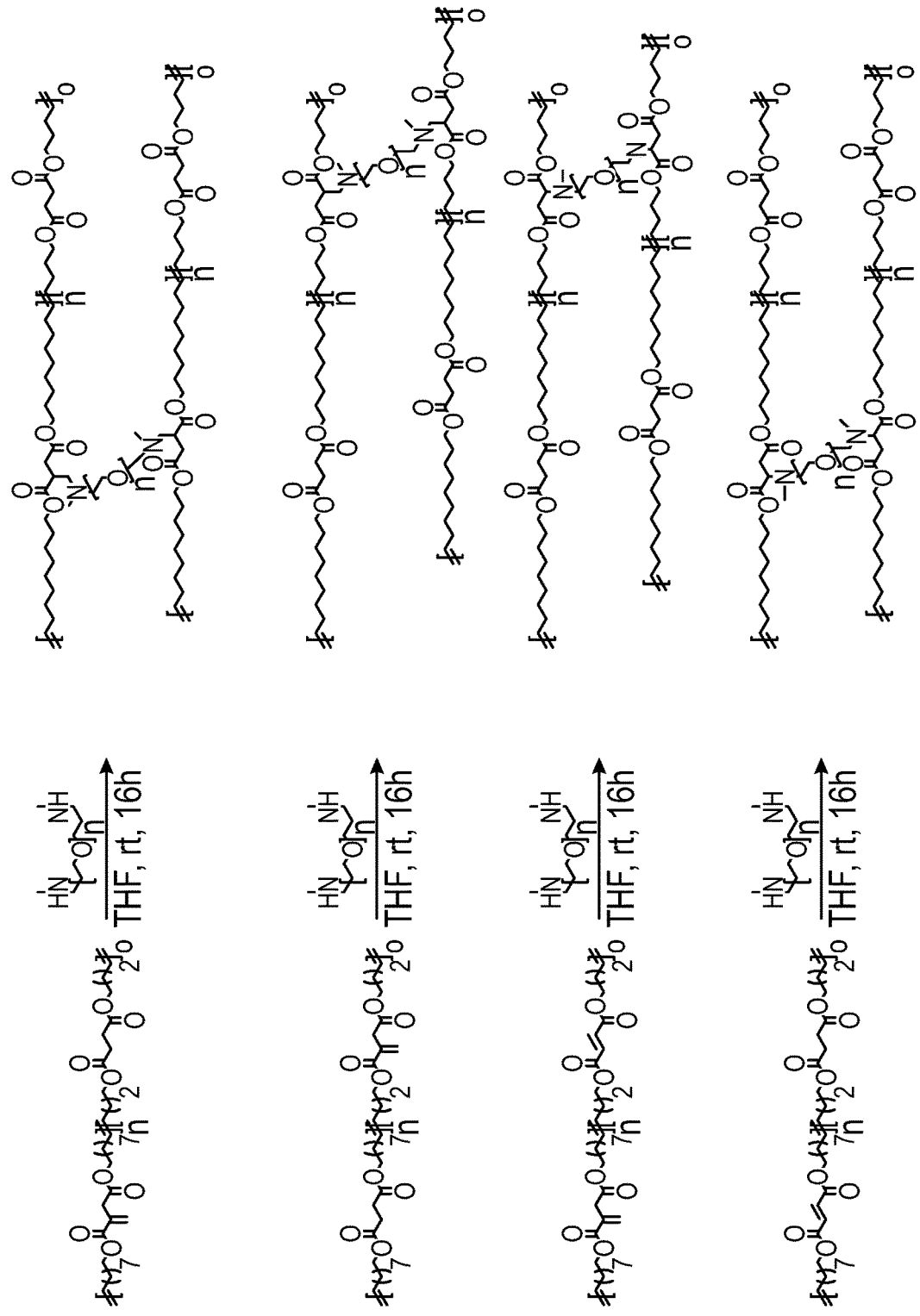

To briefly summarize the above examples, polymers with 4, 8, and 14 mol % OPD incorporation and molecular weights of around 4 K, 4600, 4420, and 3600 gmol$^{-1}$, were synthesized as nanoparticle precursors and characterized by $^1$H nuclear magnetic resonance (NMR) spectroscopy and gel permeation percentage of the crosslinking OPD group but also its concentration during the intermolecular crosslinking process is anticipated to have a significant effect on particle size. The results are summarized in FIG. 7.

Two concentrations of 2.7 and 5.4 mM were employed based on the calculated reactive monomer unit (RMU) of precursor polymers. The lower concentration corresponds to values which were established for the reported synthesis of polyester nanosponges through epoxide-amine crosslinking chemistry and the higher concentration was tested to evaluate the effect on nanoparticle size and control in nanoparticle formation.

The synthesis of the nanoparticle series was started by reacting the three polymer precursors with bis-aminooxy-PEG3 crosslinker at a 2:1 aminooxy:ketone ratio. The two concertations of the keto unit were calculated through the RMU. For example, the polymer containing 14 mol % OPD contains an average of 5 keto-bearing repeat units and has a M$_n$ equal to 3637 gmol$^{-1}$, therefore the RMU for such a polymer is 727.4 gmol$^{-1}$ per reactive functional group.

To determine the conversion of the crosslinking reactions, aliquots were taken at hourly intervals and no change in ketone conversion was observed after 2 hours determined by $^1$H NMR for the two chosen concentrations. By setting the resonance at 2.54 ppm, which corresponds to the protons alpha and beta to the ketone in the polymer backbone, as an internal standard, ketone conversion can be calculated by the reduction in intensity, and a general conversion of ca. 80% was observed. Confirmation of crosslinking was determined by the reduction in intensity of the methylene protons alpha and beta to the ketone at 2.75 ppm and an increase in the resonance of the methylene protons associated with the oxime bond at 2.54 ppm.

The second set of particles, containing the more stable alkoxyamine crosslink, was obtained by reduction of the ketoxime bond with sodium cyanoborohydride directly after nanoparticle formation in a 4 hour one-pot consecutive procedure. The post-modification was confirmed via $^1$H NMR by the reduced intensity at 2.75 ppm and the appearance of the ketoxime and alkoxyamine NPs, NP$_{KO}$ and NP$_{AA}$, respectively, were purified via dialysis to average yields of 75 wt %.

Successful formation of discrete nanoparticles was confirmed via transmission electron microscopy (TEM) and dynamic light scattering (DLS). A first NP$_{KO}$ measured at 39±10 nm in diameter and was synthesized using 4% OPD composition and 2.7 mM ketone concentration. With the same OPD content and increasing the ketone concentration to 5.4 mM the particle yielded a diameter of 58±11 nm. With 8% OPD, a range of ~80-140 nm was observed. The largest NP$_{KO}$ measured at 173±30 nm in diameter and was synthesized with 14% OPD at a 5.4 mM ketone concentration. Similar diameters were observed in DLS, and a small increase in diameter, ~20-27% was attributed to the nature of particles in solution vs. dry states.

Analysis of NPs via GPC was performed to further elucidate the relative size and distribution of these networks. The particles were soluble in organics and coould be characterized by SEC methods which is in agreement with previous studies of nanosponge materials through intermolecular crosslinking processes.

The aminooxy:ketone crosslinking ratio of 2:1 was the constant parameter throughout the series and the reactive groups per polymer were increased proportionally together with the ketone ratio, leading to the higher crosslinked nanoparticle materials.

In general, a narrow Mw/Mn (~1.3-1.85) was observed throughout all particle series, in addition to shifts toward lower retention times correlated to a larger hydrodynamic radius as size and ketone ratio increased and were in agreement with TEM and DLS data for all particles. The symmetry of the GPC traces also indicated an even distribution in particle size across the series and is confirmed by the homogeneity of particles in TEM images.

Finally, to analyze the pH responsiveness and degradation patterns of both networks in aqueous environments, NPs were suspended in buffer solution (pH 5.0 and 7.4) at 37° C. and monitored at 48 hour intervals for 10 days. Analysis of absolute molecular weight via static light scattering (SLS) was performed to determine percent mass remaining of NPs at each time point and calculated as a function of total NP mass determined prior to degradation studies.

As expected, NP$_{KO}$ exhibited a faster rate of degradation than NP$_{AA}$ in both neutral and acidic conditions due to the acid-labile nature of the oxime bond. Prior to degradation, NP$_{KO}$ MW was determined to be 198 kDa. After 10 days of exposure to acidic buffer, MW was reduced to ~43 kDa, indicating a total mass loss of 78.16% and an average 7.82% per day. Comparatively, analysis of NP$_{AA}$ indicated a 260 kDa starting MW, yet was only reduced to 132 kDa after 10 days in an acidic environment. This particle exhibited a total mass loss of 49.23% and 4.92% average per day. In PBS, NP$_{KO}$ exhibited the final MW of ~70 kDa, an average loss of 5.98% daily while NP$_{AA}$ measurements indicated a final MW of 159.5 kDa, averaging 3.87% daily mass loss. These results indicating a tunable degradation network based on the pH and chemical nature of the crosslinks.

To examine the effect of the nanostructure on the drug release, Brefeldin A (BFA), a natural product that effects the function of the ER-Golgi network and leading to DNA fragmentation, and a new target in the apoptosis of human cancer cell lines, was selected for incorporation into the particles. The drug has shown high potency in HL60 and K562 leukemia cells as well as in HT-29 colon carcinoma cells, cell lines which are p53 null. Furthermore, BFA enhances the efficacy of widely used drugs such as docetaxel as tested on prostate cancer cells.

ued release through 7-13 days or longer using practical synthetic parameters and fabrication methods.

Example 12

Double Emulsion Procedure of Ketoxime Particles ($P_{KO}$).

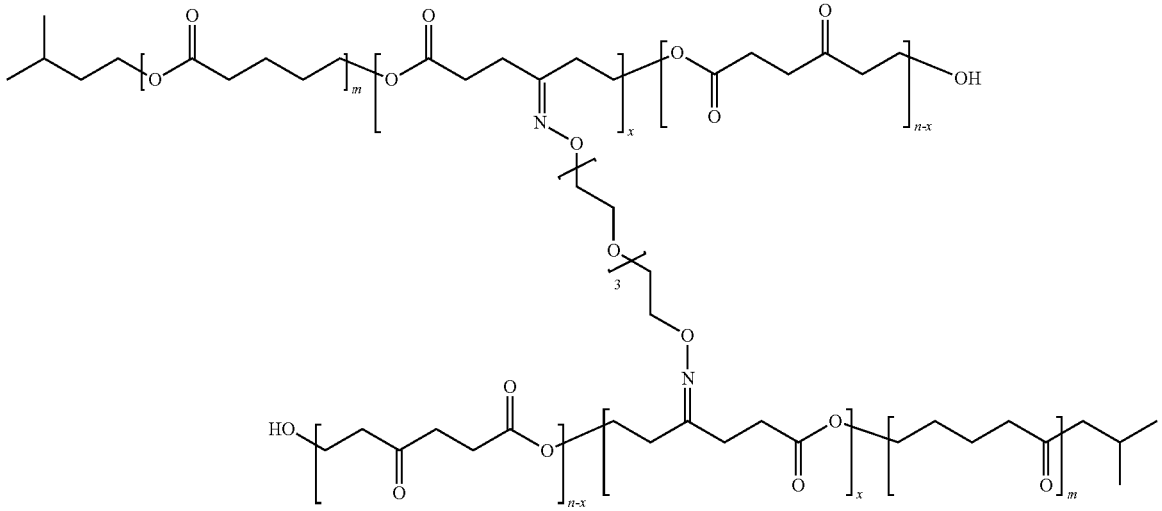

BFA was incorporated into the $NP_{KO}$ and $NP_{AA}$ synthesized from 8% OPD precursor.

The drug loading was determined via HPLC analysis to be 19.6 wt % BFA with a drug loading efficiency of 98% for BFA-$NP_{KO}$ and 13.5 wt % BFA with a 68% drug loading efficiency for BFA-$NP_{AA}$. The release of BFA from BFA-$NP_{KO}$ and BFA-$NP_{AA}$ was surveyed in identical aqueous media used in the previous degradation study with pH 5.0 and 7.4. $NP_{AA}$ in pH 5.0 exhibited the fastest release rate of the series, releasing 50% cargo in 24 hours and 100% in 7 days. Both $NP_{KO}$ and $NP_{AA}$ in pH 7.4 showed a medium release with similarly observed rates with $NP_{AA}$ exhibiting a more linear trend. $NP_{KO}$ in pH 7.4 reached 50% in 48 hours and 96% in 11 days. $NP_{AA}$ in pH 7.4 released 50% between 3-5 days and 100% between 9-11 days. These data correspond to the trends observed in the hydrolytic degradation of each particle. However, the release of BFA from $NP_{KO}$ exhibited the slowest release of all particle systems which was not anticipated based on the prior degradation analysis.

To seek a rational for contrary release kinetics of the $NP_{KO}$ particle, we hypothesized that the particle during the degradation process yields functional groups such as aminooxy functionalities and keto units that interact with the drug and result in an increased binding of the drug to the degrading particle. To test this hypothesis, no interaction could be detected for drug and aminooxy crosslinker, but a physical mixture of drug and precursor polymer yielded a reduced signal by HPLC after 72 hours as well as the appearance of large particulates, which indicate an interaction of regenerated keto groups with BFA. The much slower release rate of the $NP_{KO}$ in acidic conditions could be potentially useful for release of highly potent chemotherapeutics to the extracellular matrix of tumors, known to exhibit lower pH. Release profiles at neutral pH provide a tailorable range with medium release profiles. These nanonetworks demonstrate the ability to precisely tune drug release profiles for fast, medium, or slow rates with contin- A 1 wt % stock solution of the surfactant, 90% hydrolyzed polyvinyl alcohol (PVA), in deionized water was made by dissolving the PVA at high stirring and 75° C. heating for 2 hours. Another PVA water solution was made by dilution to result in a 0.3 wt % solution. 50 mg of the polymer 8% or 14% P(VL-OPD) was weighed into a 1-dram vial and dissolved in 2 mL of dichloromethane (DCM). In a separate vial, the cross-linker aminooxy-PEG3 (5 or 10 equivalents to ketone functionality) was added and also dissolved in 2 mL of DCM. In a 25 mL round bottom flask, the remaining DCM to yield a concentration of 10.8 mM (ketone functionality in mmol to mL DCM) was added along with the polymer solution. At a high stirring vortex, the cross-linker solution was added by injecting all at once and directly to the vortex. The organic solution was allowed to stir for 5 minutes. The organic phase was then added dropwise to a round-bottom flask containing the 1 wt % PVA in water solution in a 1:1 ratio to the organic phase and allowed to stir for 5 more minutes. The resulting initial emulsion solution was then transferred to a 0.3 wt % PVA solution (10 times the amount of the 1 wt %) and stirred at ambient temperature for 6 hours until the DCM evaporated. The final emulsion solution was then transferred to centrifuge tubes and centrifuged at highest speed for 40 minutes and washed twice with deionized water. The emulsion in water was then lyophilized overnight to remove any remaining water. The particles were re-dissolved in 3:2 DCM:isopropyl alcohol (IPA) solution and solvent was evaporated via rotovap and placed on high vacuum pump overnight to yield a yellow waxy solid.

Example 13

Procedure for encapsulation of Class IX drugs into Ketoxime Microparticles via emulsion. A 1 wt % stock solution of the surfactant, 90% hydrolyzed polyvinyl alcohol (PVA), in deionized water was made by dissolving the PVA at high stirring and 75° C. heating for 2 hours. Another PVA water solution was made by dilution to get 0.3 wt % solution. The organic solution was made in a 25 mL round bottom flask. 50 mg of the polymer 8% or 14% P(VL-OPD) and 15 mg of the Class IX drug were weighted out in a 1-dram vial and dissolved in 2 mL of dichloromethane (DCM). In a separate vial 10 or 5 equivalents of the cross-linker aminooxy-PEG3 was weighed and also dissolved in 2 mL of DCM. In the flask, the remaining amount of DCM to yield a concentration of 10.8 mM was added as long with the polymer solution. At the highest stirring setting the crosslinked was added by injecting all at once and close to the vortex. The organic solution was allowed to stir for 5 minutes and then added in a steady dropwise to a round-bottom flask containing the 1 wt % PVA in water solution in a 1:1 to the organic solution and allowed to stir for 5 more minutes. Then the emulsion was transferred to the 0.3 wt % PVA solution and stirred at ambient temperature for 6 hours until the DCM evaporates. The emulsion was transfered to centrifugal tubes and centrifuge at highest speed for 40 minutes and washing with water twice. The emulsion in water was then freezed and placed on the lyophilizer overnight to get rid of the water. The drug-loaded particles were redissolved in 3:2 DCM: isopropyl alcohol (IPA) and solvent was evaporated via rotovap and placed on high vacuum pump overnight.

Example 14

Synthesis of Partially Reduced Ketoxime/Alkoxyamine Particles. Poly(δ-valerolactone-co-2-oxepane-1,5-dione) (300 mg, 0.213 mmol) with an 8% ketone functionality was solubilized in anhydrous dichloromethane (DCM) to a concentration of 2.7 mM in a 50 mL round bottom flask containing a magnetic stir bar. Bisaminooxy-PEG-3 (48 mg, 0.213 mmol, 1 equiv.) was also solubilized in no more than 2 mL DCM and transferred rapidly and all at once with stirring at the highest setting to the round bottom flask and allowed to react for 2 hours at room temperature. After 2 hours, sodium cyanoborohydride (6.69 mg, 0.11 mmol, 0.5 equiv.) and a catalytic amount of saturated sodium bicarbonate solution (250 µL) were added to the reaction flask and allowed to react for an additional 2 hours at room temperature. The reaction mixture was transferred to Thermo Scientific™ SnakeSkin™ 10K MWCO Dialysis tubing and dialyzed against Methanol:DCM 1:1 for 48 hours with 3-4 solvent changes per day. The solution was filtered with a 0.45 µm PTFE syringe filter to remove solid salt particulates and solvent was removed via rotary evaporation. The product was dried in vacuo and 51% yield was obtained. 1H NMR (400 MHz, CDCl3): δ 0.90 (d, 6H); 1.6-1.75 (m); 2.23-2.43 (m); 2.25-2.7 (m); 2.7-2.84 (m); 3.4 (t); 3.65 (m); 4.0 (t); 4.3-4.4 (m). 13C NMR (600 MHz, CDCl3): δ 21.32, 25.53, 28.00, 33.62, 63.85, 67.88, 173.26.

Example 15

Encapsulation of Doxorubicin into Partially Reduced Ketoxime/Alkoxyamine Nanoparticles. Doxorubicin (DOX) (14.1 mg) was solubilized in dimethyl sulfoxide (DMSO) (30 µL) in a 1.5 mL centrifuge tube. NPs (47.5 mg, 8% OPD, 2.7 mM, ~80 nm) were added to the DOX centrifuge tube and an additional 150 µL DMSO were added to solubilize the mixture. The mixture was split equally into 6 1.5 mL centrifuge tubes, approximately 25 µL each. Cell culture grade water containing 0.1% D-α-tocopherol polyethylene glycol 1000 succinate (1 mL) was added to each centrifuge tube and vortexed to induce DOX encapsulation. D-α-tocopherol polyethylene glycol 1000 succinate was added to coat the particles during encapsulation and aid in resuspension in aqueous media during drug release studies. The mixture was then centrifuged at 14000 RPM for 40 minutes. The supernatant was decanted, fresh cell culture grade water (1 mL) was added to the particle pellet and vortexed until particles were resuspended. Centrifugation was repeated at 14000 RPM for 40 minutes, then the supernatant was decanted to remove any unincorporated drug. Cell culture grade water (0.5 mL) was added to the mixture, frozen, and lyophilized to produce DOX-loaded nanoparticles (DOX-NP). HPLC analysis confirmed encapsulation of DOX at an average of 12.5 wt % with 55.0% efficiency.

Example 16

In Vitro Release of Doxorubicin from Partially Reduced Ketoxime/Alkoxyamine Nanoparticles. DOX-loaded nanoparticles were suspended in 1 mL of either sodium acetate-acetic acid buffer (pH 5) or PBS (pH 7.4) containing 0.1% v/v Tween-80 as a surfactant. The suspended DOX-NP were transferred to Float-a-Lyzer® dialysis pod (MWCO: 1000 kD). The pods were placed into 50-mL Falcon tube containing 18 mL of the corresponding release media. Falcon tubes were placed in an oil bath at 37° C. and media was stirred constantly using a magnetic stir bar. Samples of 150 µL were collected from the sink after 1, 2, 4, 6, 24, 48, 72 hours and every two days following. An equal amount of fresh media was added to the sink after each sample withdrawal to maintain sink conditions. The amount of DOX released was quantified using HPLC at 475 nm and 35° C. with a gradient solvent system of 100% A to 30% A:70% B over 12 minutes. Solvent A was water with 1% trifluoracetic acid (TFA), and solvent B was 90% acetonitrile/10% water with 1% TFA.

The results are summarized in Tables 2, 3 and 4 below and in FIG. 8.

TABLE 2

Four $P_{KO}$ with their resulting diameters as measured by TEM.

| Entry | $M_n^a$, (g/mol) | % OPD$^a$ | $M^b$ (mmol/mL) | Cross-linker eq | Diameter$_{TEM}$ (nm) |
|---|---|---|---|---|---|
| $P_{KO}$ 1 | 3722 | 8 | 0.0108 | 5 | 294 ± 252 |
| $P_{KO}$ 2 | 3722 | 8 | 0.0108 | 10 | 533 ± 402 |
| $P_{KO}$ 3 | 5514 | 14 | 0.0108 | 5 | 415 ± 1102 |
| $P_{KO}$ 4 | 5514 | 14 | 0.0108 | 10 | 1378 ± 666 |

$^a$% OPD and $M_n$ determined by 400 MHz $^1$H NMR in CDCl$_3$.
$^b$Concentration of ketone functionality in mmol to mL of dichloromethane.

TABLE 3

Six $NP_{KO}$ with their resulting diameters as measured by TEM.

| Entry | $M_n^a$, (g/mol) | % OPD$^a$ | $M^b$ (mmol/mL) | Cross-linker eq | Diameter$_{TEM}$ (nm) |
|---|---|---|---|---|---|
| $NP_{KO}$ 1 | 5514 | 14 | 0.0054 | 5 | 244 ± 116 |
| $NP_{KO}$ 2 | 5514 | 14 | 0.0054 | 10 | 512 ± 249 |
| $NP_{KO}$ 3 | 5514 | 14 | 0.0081 | 5 | 192 ± 95 |
| $NP_{KO}$ 4 | 5514 | 14 | 0.0081 | 10 | 544 ± 344 |
| $NP_{KO}$ 5 | 5514 | 14 | 0.0108 | 5 | 374 ± 174 |
| $NP_{KO}$ 6 | 5514 | 14 | 0.0108 | 10 | 291 ± 131 |

$^a$% OPD and $M_n$ determined by 400 MHz $^1$H NMR in CDCl$_3$.
$^b$Concentration of ketone functionality in mmol to mL of dichloromethane.

TABLE 4

Four $NP_{KO}$ with their resulting diameters as measured by TEM comparing reaction time.

| Entry | $M_n$,[a] (g/mol) | % OPD[a] | $M$[b] (mmol/mL) | Reaction time (hours) | Cross-linker eq | Diameter$_{TEM}$ (nm) |
|---|---|---|---|---|---|---|
| $NP_{KO}$ 1 | 5514 | 14 | 0.0054 | 2 | 5 | 244 ± 116 |
| $NP_{KO}$ 2 | 5514 | 14 | 0.0054 | 2 | 10 | 512 ± 249 |
| $NP_{KO}$ 7 | 5514 | 14 | 0.0054 | 4 | 5 | 183 ± 105 |
| $NP_{KO}$ 8 | 5514 | 14 | 0.0054 | 4 | 10 | 315 ± 258 |

[a]% OPD and $M_n$ determined by 400 MHz $^1$H NMR in CDCl$_3$. [b]Concentration of ketone functionality in mmol to mL of dichloromethane.

Example 17

Synthesis of Di(9-decenyl) Itaconate (DDI).

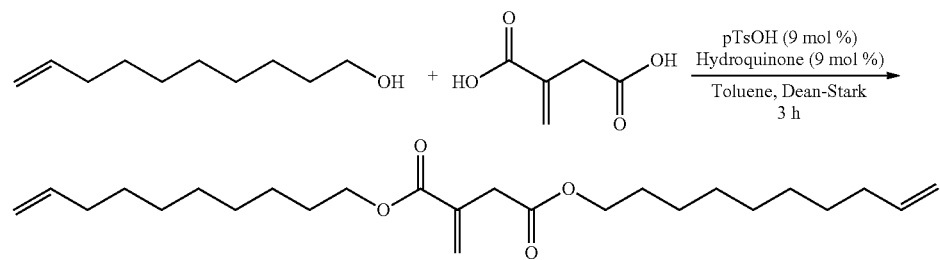

Into a 100 mL round-bottom flask, itaconic acid (3.90 grams, 30 mmol), 9-decenol (10.22 grams, 60 mmol), p-toluenesulfonic acid (0.456 grams, 2.65 mmol), hydroquinone (0.29 grams, 2.68 mmol), and toluene (45 mL) were transferred and then fitted with a Dean-Stark trap. The mixture was refluxed under vigorous stirring for 3 hours. The reaction solution was then cooled to room temperature and washed with 90 mL of deionized water three times. The product was dried over magnesium sulfate and concentrated by rotary evaporation. The obtained crude product was purified by silica column chromatography on the Biotage using a SNAP Ultra 50 g silica column (hexanes/ethyl acetate=5/1) to afford the final product as a colorless oil (66% yield). $^1$H NMR (400 MHz, CDCl$_3$), δ (TMS, ppm): 6.32 (s, 1H), 5.82 (m, 2H), 5.69 (s, 1H), 4.94 (m, 4H), 4.14 (t, 2H), 4.08 (t, 2H), 3.33 (s, 2H), 2.03 (m, 4H), 1.77-1.55 (m, 4H), 1.46-1.21 (m, 20H).

Example 18

Synthesis of Di(4-pentenyl) Succinate (DPS).

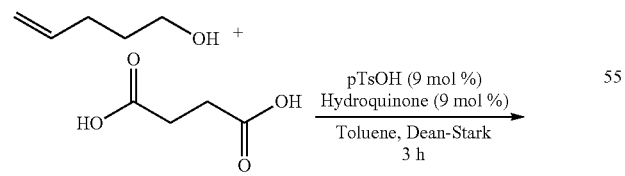

-continued

Into a 100 mL round-bottom flask, succinic acid (3.50 grams, 30 mmol), 4-pentenol (5.17 grams, 60 mmol), p-toluenesulfonic acid (0.456 grams, 2.65 mmol), hydroquinone (0.29 grams, 2.68 mmol), and toluene (45 mL) were transferred and then fitted with a Dean-Stark trap. The mixture was refluxed under vigorous stirring for 3 hours. The reaction solution was then cooled to room temperature and washed with 90 mL of deionized water three times. The product was dried over magnesium sulfate and concentrated by rotary evaporation. The obtained crude product was purified by silica column chromatography on the Biotage using a SNAP Ultra 50 g silica column (hexanes/ethyl acetate=9/1) to afford the final product as a colorless oil (77% yield). 1H NMR (400 MHz, CDCl3), δ (TMS, ppm): 5.81 (m, 2H), 5.01 (m, 4H), 4.10 (t, 4H), 2.63 (s, 4H), 2.11 (m, 4H), 1.73 (m, 4H).

Example 19

Synthesis of Di(9-decenyl) Succinate (DDS).

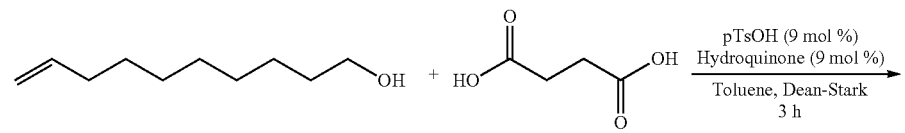

-continued

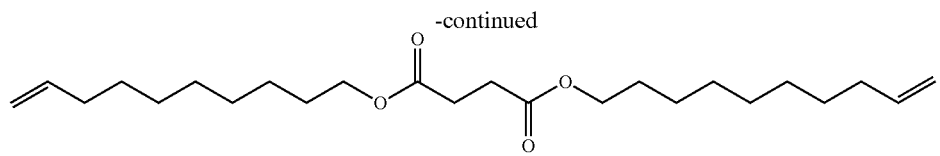

Into a 100 mL round-bottom flask, succinic acid (3.50 grams, 30 mmol), 9-decenol (10.22 grams, 60 mmol), p-toluenesulfonic acid (0.456 grams, 2.65 mmol), hydroquinone (0.29 grams, 2.68 mmol), and toluene (45 mL) were transferred and then fitted with a Dean-Stark trap. The mixture was refluxed under vigorous stirring for 16 hours. The reaction solution was then cooled to room temperature and washed with 90 mL of deionized water three times. The product was dried over magnesium sulfate and concentrated by rotary evaporation. The obtained crude product was purified by silica column chromatography on the Biotage using a SNAP Ultra 50 g silica column (hexanes/ethyl acetate=5/1) to afford the final product as a colorless oil (73% yield 1H NMR (400 MHz, CDCl3), δ (TMS, ppm): 5.82 (m, 2H), 4.94 (m, 4H), 4.07 (t, 4H), 2.62 (s, 4H), 1.77-1.55 (m, 4H), 1.46-1.21 (m, 20H).

Example 20

Synthesis of Di(9-decenyl) Fumarate (DDF).

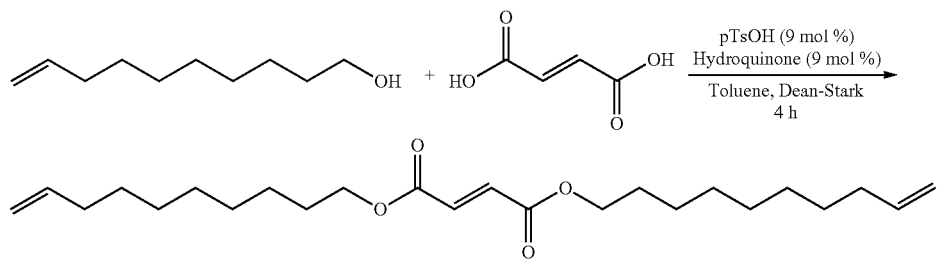

Into a 100 mL round-bottom flask, fumaric acid (3.48 grams, 30 mmol), 9-decenol (10.22 grams, 60 mmol), p-toluenesulfonic acid (0.456 grams, 2.65 mmol), hydroquinone (0.29 grams, 2.68 mmol), and toluene (45 mL) were transferred and then fitted with a Dean-Stark trap. The mixture was refluxed under vigorous stirring for 16 hours. The reaction solution was then cooled to room temperature and washed with 90 mL of deionized water three times. The product was dried over magnesium sulfate and concentrated by rotary evaporation. The obtained crude product was purified by silica column chromatography on the Biotage using a SNAP Ultra 50 g silica column (hexanes/ethyl acetate=5/1) to afford the final product as a colorless oil (72% yield). $^1$H NMR (400 MHz, CDCl$_3$), δ (TMS, ppm): 6.84 (s, 2H), 5.82 (m, 2H), 4.19 (t, 4H), 2.04 (m, 4H), 1.77-1.55 (m, 4H), 1.46-1.21 (m, 20H).

Example 21

Synthesis of Di(4-pentenyl) Itaconate (DPI)

-continued

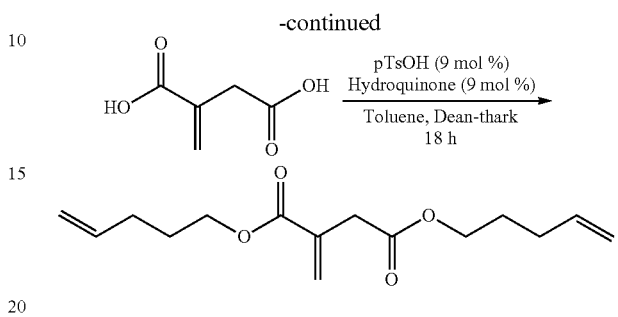

Into a 100 mL round-bottom flask, itaconic acid (3.90 grams, 30 mmol), 4-pentenol (5.17 grams, 60 mmol), p-toluenesulfonic acid (0.456 grams, 2.65 mmol), hydroquinone (0.29 grams, 2.68 mmol), and toluene (45 mL) were transferred and then fitted with a Dean-Stark trap. The mixture was refluxed under vigorous stirring for 18 hours. The reaction solution was then cooled to room temperature and washed with 90 mL of deionized water three times. The product was dried over magnesium sulfate and concentrated by rotary evaporation. The obtained crude product was purified by silica column chromatography on the Biotage using a SNAP Ultra 50 g silica column (hexanes/ethyl acetate=9/1) to afford the final product as a colorless oil (57% yield). 1H NMR (400 MHz, CDCl3), δ (TMS, ppm): 6.32 (s, 1H), 5.82 (m, 2H), 5.69 (s, 1H), 4.94 (m, 4H), 4.14 (t, 2H), 4.08 (t, 2H), 3.33 (s, 2H), 2.03 (m, 4H), 1.77-1.55 (m, 4H).

Example 22

Synthesis of di-(4-pentenyl)-fumarate (DPF)

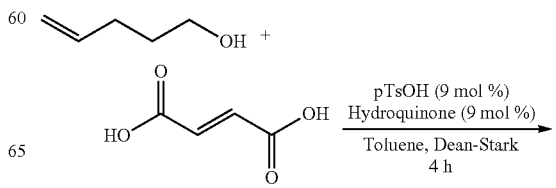

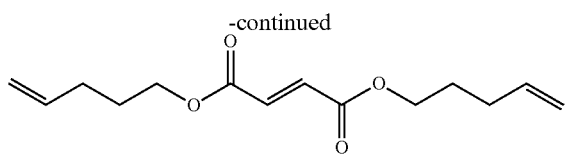

Into a 100 mL round-bottom flask, fumaric acid (3.48 grams, 30 mmol), 4-pentenol (5.17 grams, 60 mmol), p-toluenesulfonic acid (0.456 grams, 2.65 mmol), hydroquinone (0.29 grams, 2.68 mmol), and toluene (45 mL) were transferred and then fitted with a Dean-Stark trap. The mixture was refluxed under vigorous stirring for 18 hours. The reaction solution was then cooled to room temperature and washed with 90 mL of deionized water three times. The product was dried over magnesium sulfate and concentrated by rotary evaporation. The obtained crude product was purified by silica column chromatography on the Biotage using a SNAP Ultra 50 g silica column (hexanes/ethyl acetate=9/1) to afford the final product as a colorless oil (17% yield 1H NMR (400 MHz, CDCl3), δ (TMS, ppm): 6.84 (s, 2H), 5.75 (m, 2H), 4.94 (m, 4H), 4.15 (t, 2H), 4.08 (t, 2H), 2.15 (m, 4H), 1.74 (m, 4H).

Example 23

General Procedure for ADMET Copolymerization

Monomer 1 and monomer 2 (1:1 molar ratio), Grubb's 1st generation catalyst (G-I) and DCM were sequentially transferred into a flame dried 25 mL three neck round bottom flask, which was equipped with a stir bar and reflux condenser. The mixture was heated in an oil bath set at 40° C. A continuous nitrogen flow was provided through one neck to remove the generated ethylene which was released through the neck on the opposite side. DCM was evaporated, and the mixture became semisolid within several hours. The polymerization was continued for at least 24 hours. The reaction was quenched with a large excess of ethyl vinyl (about 15 mL). The mixture was precipitated into cold methanol (250 mL). The product was obtained from DCM after centrifugation and vacuum dryness overnight.

Example 24

ADMET Polymerization of P(DDI-co-DPS).

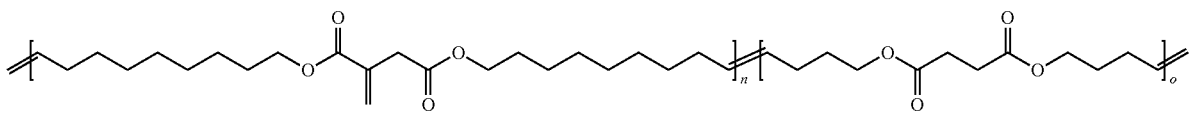

The general procedure for ADMET polymerization was followed using monomer DDI (1.23 grams, 1.46 mmol), co-monomer DPS (743 mg, 1.46 mmol), G-I (23.9 mg, 29 μmol), and DCM (1.5 mL). A grayish-white solid was obtained in 43% yield. A $^1$H NMR spectrum of P(DDI-co-DPS) is provided as FIG. 9.

Example 25

ADMET Polymerization of P(DDF-co-DPS).

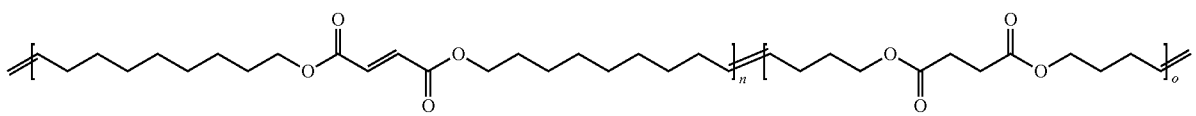

The general procedure for ADMET polymerization was followed using monomer DDF (1.22 grams, 3.1 mmol), co-monomer DPS (788 mg, 3.1 mmol), G-I (25.5 mg, 31 μmol), and DCM (1.6 mL). A grayish-white solid was obtained in 59% yield. A $^1$H NMR spectrum of P(DDF-co-DPS) is provided as FIG. 10.

Example 26

ADMET Polymerization of P(DDS-co-DPI).

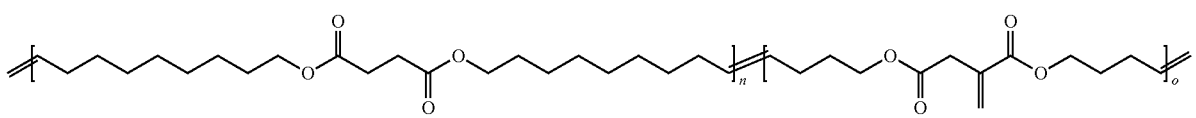

The general procedure for ADMET polymerization was followed using monomer DDS (1.2 grams 3.02 mmol), co-monomer DPI (804 mg, 3.02 mmol), G-I (25 mg, 30 μmol), and DCM (4.53 mL). A brown-black viscous liquid was obtained in 52% yield. A $^1$H NMR spectrum of P(DDS-co-DPI) is provided as FIG. 11.

Example 27

ADMET Polymerization of P(DDS-co-DPF).

50 mg of the polymer P(DDS-co-DPF) were weighted into a 1-dram vial and solubilized in 2 mL of THF. In a separate 1-dram vial, Bis-PEG5-Thiol (1, 4, or 8 equivalents to activated alkene) were added and dissolved in 2 mL of THF. In a 25 mL round-bottom flask equipped with a magnetic stir bar, the additional THF was added to obtain a final concentration of 5.4 mM (concentration of activated alkene functionality in mmol to mL of DCM). The polymer solution was added to the flask and placed under an Argon balloon. At high vortex stirring, the cross-linker solution was added all at once to the vortex and the reaction was allowed

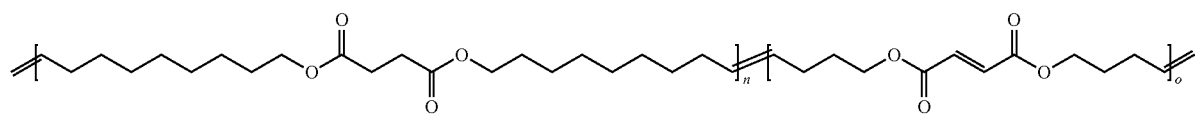

The general procedure for ADMET polymerization was followed using monomer DDS (1.2 grams, 3.1 mmol), co-monomer DPF (782 mg, 3.1 mmol), G-I (25.5 mg, 31 μmol), and DCM (3.1 mL). A brown-black viscous liquid was obtained in 50% yield. A $^1$H NMR spectrum of P(DDS-co-DPF) is provided as FIG. 12.

FIGS. 13 and 14 summarize GPC analyses of P(DDI-co-DPS) and P(DDS-co-DPI), respectively.

to stir at ambient temperature. After 16 hours, the reaction was quenched by adding methylacrylate (5 equivalents to thiol added) and allowed to stir for an additional 3 hours. The reaction mixture was then transferred directly into Thermo Scientific™ SnakeSkin™ 10K MWCO Dialysis Tubing and dialyzed against THF for 48 hours with approximately 3-4 changes of solvent per day. The solvent was removed via rotary evaporation. The product was dried in vacuo.

TABLE 5

GPC and NMR analysis of polymers synthesized via ADMET polymerization

| Polymer | Monomer feed ratio | Monomer incorporation[a] | Reaction time (hours) | $M_{n,\ theo}$ (g/mol) | $M_n$[b] (g/mol) | $M_n/M_w$[b] |
|---|---|---|---|---|---|---|
| P(DDI-co-DPS) | 50:50 | 57/43 | 17 | 50,000 | 12000 | 1.96 |
| P(DDI-co-DPS) | 50:50 | 57/43 | 18 | 50,000 | 7,600 | 1.37 |
| P(DDI-co-DPS) | 50:50 | 51/49 | 24 | 50,000 | 12000 | 1.33 |
| P(DDF-co-DPS) | 50:50 | 50/50 | 17 | 50,000 | 8,300 | 2.89 |
| P(DDF-co-DPS) | 50:50 | 51/49 | 63 | 50,000 | 13,000 | 2.23 |
| P(DDS-co-DPI) | 50:50 | 56/44 | 24 | 50,000 | 9,000 | 1.31 |
| P(DDS-co-DPF) | 50:50 | 51/49 | 24 | 50,000 | 7,000 | 1.51 |

[a]Monomer incorporation determined by 400 MHz $^1$H NMR in CDCl$_3$. [b]Molecular weight and polydispersity measured by GPC at 40° C. in THF and a flow rate of 1 mL/min using ToSOH EcoSEC HLC-8320GPC system equipped with TSKgel H$_{HR}$ columns (7.8 × 300 mm G5000H$_{HR}$, G4000H$_{HR}$, and G3000H$_{HR}$).

Example 28

General Procedure for Thiol-Michael Addition Particle Formation

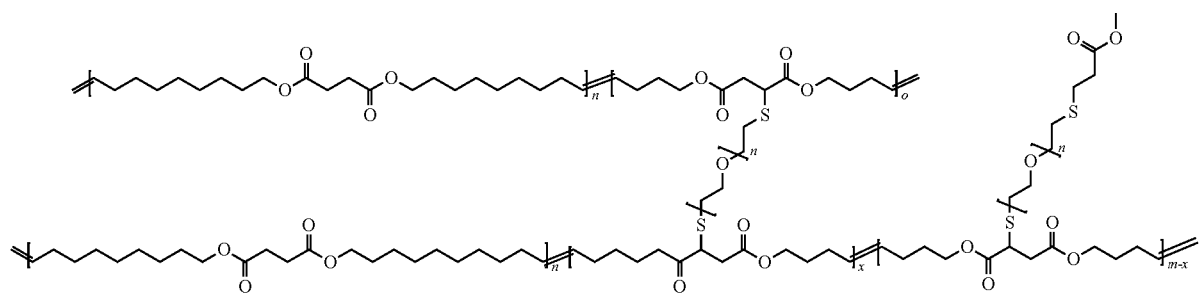

TABLE 6

Two thiol-Michael addition particles (tMP) with their resulting diameters as measured by TEM

| Entry | $M_{n,GPC}{}^{a}$ (g/mol) | $M_w/M_n{}^{a}$ | % activated alkene[b] | $M^c$ (mmol/mL) | Cross-linker eq | Reaction Time (hours) | Diameter$_{TEM}$ (nm) |
|---|---|---|---|---|---|---|---|
| tMP 1 | 7,000 | 1.51 | 49 | 0.0054 | 1 | 16 | 141 ± 45 |
| tMP 2 | 7,000 | 1.51 | 49 | 0.0054 | 4 | 16 | 210 ± 53 |

[a]Molecular weight precursor polymer used measured by GPC with THF as the eluent at 40° C. with a flow rate of 1 mL/min. [b]Percent functionalization of the activated alkene in the polymer scaffold as determined by the $^1$H NMR integration. [c]Concentration of ketone functionality in mmol to mL of dichloromethane.

Example 29

General Procedure for Aza-Michael Addition Particle Formation

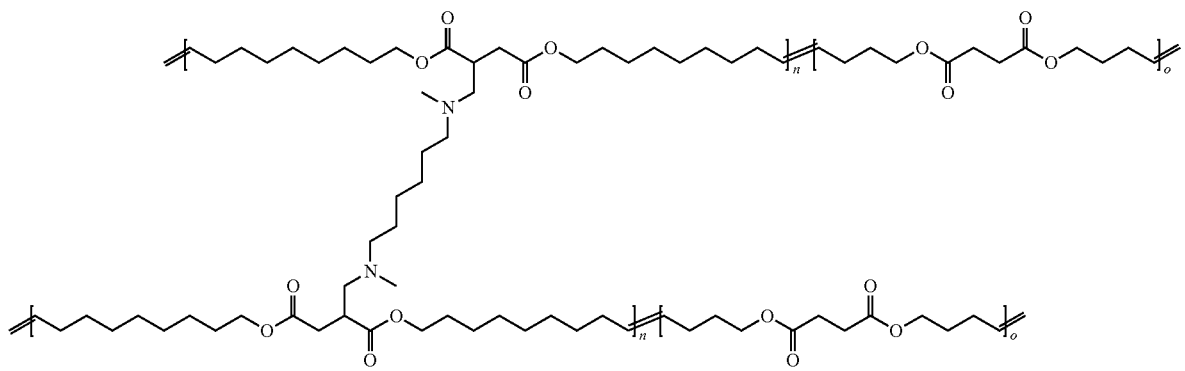

50 mg of the polymer P(DDI-co-DPS) were weighted into a 1-dram vial and solubilized in 2 mL of THF. In a separate 1-dram vial, N'N'-dimethyl-1,6-hexadiamine (1, 4, or 8 equivalents to activated alkene) were added and dissolved in 2 mL of THF. In a 25 mL round-bottom flask equipped with a magnetic stir bar, the additional THF was added to obtain a final concentration of 5.4 Mm (concentration of activated alkene functionality in mmol to mL of DCM). The polymer solution was added to the flask and placed under an Argon balloon. At high vortex stirring, the cross-linker solution was added all at once to the vortex and the reaction was allowed to stir at ambient temperature. After 16 hours, the reaction mixture was transferred directly into Thermo Scientific™ SnakeSkin™ 10K MWCO Dialysis Tubing and dialyzed against THF for 48 hours with approximately 3-4 changes of solvent per day. The solvent was removed via rotary evaporation. The product was dried in vacuo.

Example 30

General Procedure for Particle Formation

Polymer was weighted into a 1-dram vial and solubilized in 2 mL of THF. In a separate 1-dram vial, the cross-linker (from the list below in either 1, 4, or 8 equivalents to activated alkene) were added and dissolved in 2 mL of THF. In a 25 mL round-bottom flask equipped with a magnetic stir bar, the additional THF was added to obtain the desired final concentration (concentration of activated alkene functionality in mmol to mL of DCM). The polymer solution was added to the flask and placed under an Argon balloon. At high vortex stirring, the cross-linker solution was added all at once to the vortex and the reaction was allowed to stir at ambient temperature. Once the reaction was complete, the reaction mixture was then transferred directly into Thermo Scientific™ SnakeSkin™ 10K MWCO Dialysis Tubing and dialyzed against THF for 48 hours with approximately 3-4 changes of solvent per day. The solvent was removed via rotary evaporation. The product was dried in vacuo.

Representative aza-Michael Addition Particle Formation Reactions are summarized in FIGS. 15-19.

TABLE 7

Four aza-Michael addition particles (aMP) with their resulting diameters as measured by TEM.

| Entry | $M_{n,GPC}{}^{a}$ (g/mol) | $M_w/M_n{}^{a}$ | % activated alkene[b] | $M^c$ (mmol/mL) | Cross-linker eq | Reaction Time (hours) | Diameter$_{TEM}$ (nm) |
|---|---|---|---|---|---|---|---|
| aMP 1 | 7,600 | 1.37 | 57 | 0.0054 | 4 | 16 | 121 ± 58 |
| aMP 2 | 12,000 | 1.96 | 57 | 0.0054 | 4 | 20 | 500 ± 272 |
| aMP 3 | 12,000 | 1.96 | 57 | 0.0054 | 1 | 16 | 73 ± 25 |
| aMP 4 | 12,000 | 1.96 | 57 | 0.0054 | 4 | 16 | 127 ± 47 |
| aMP 5 | 12,000 | 1.96 | 57 | 0.0054 | 8 | 16 | 116 ± 23 |

[a]Molecular weight precursor polymer used measured by GPC with THF as the eluent at 40° C. with a flow rate of 1 mL/min.
[b]Percent functionalization of the activated alkene in the polymer scaffold as determined by the $^1$H NMR integration.
[c]Concentration of ketone functionality in mmol to mL of dichloromethane.

While the above description contains many specific details of methods in accordance with this disclosure, these specific details should not be construed as limitations on the scope of the disclosure, but merely as exemplifications of preferred embodiments thereof. Those skilled in the art will envision many other possible variations that are all within the scope and spirit of the disclosure.

What is claimed is:
1. A therapeutic composition comprising:
a modified polyester having functional groups within the polyester backbone comprising
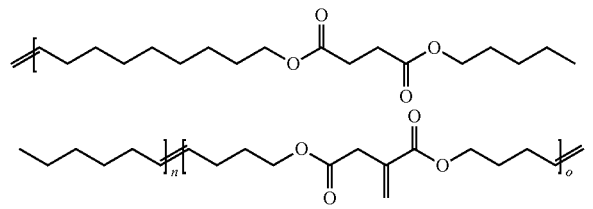
poly(Di(9-decenyl)Succinate-co-Di(4-pentenyl)Itaconate;

a secondary diamine crosslinking agent; and a bioactive agent comprising Brefeldin A, wherein the crosslinking agent reacts with the functional groups within the polyester backbone to form bonds between multiple polyester backbones, thereby forming a nanoparticle.

2. The therapeutic composition of claim 1, wherein the nanoparticle reacts with other nanoparticles to form a nanosponge possessing the bioactive agent.

3. The therapeutic composition of claim 2, wherein the nanosponge possesses the bioactive agent in an amount from about 1% by weight of the nanosponge to about 25% by weight of the nanosponge.

* * * * *